United States Patent
Park et al.

(10) Patent No.: US 8,063,229 B2
(45) Date of Patent: Nov. 22, 2011

(54) ANTIFUNGAL TRIAZOLE DERIVATIVES, METHOD FOR THE PREPARATION THEREOF AND PHARMACEUTICAL COMPOSITION CONTAINING SAME

(75) Inventors: Joon Seok Park, Yongin-si (KR); Kyung A Yu, Suwon-si (KR); Yun Soo Yoon, Seoul (KR); Mi Ryeong Han, Anyang-si (KR)

(73) Assignee: Daewoong Pharmaceutical Co., Ltd., Seongnam-si (KR)

( * ) Notice: Subject to any disclaimer, the term of this patent is extended or adjusted under 35 U.S.C. 154(b) by 227 days.

(21) Appl. No.: 12/520,945

(22) PCT Filed: Dec. 28, 2007

(86) PCT No.: PCT/KR2007/006961
§ 371 (c)(1),
(2), (4) Date: Jun. 23, 2009

(87) PCT Pub. No.: WO2008/082198
PCT Pub. Date: Jul. 10, 2008

(65) Prior Publication Data
US 2010/0063285 A1    Mar. 11, 2010

(30) Foreign Application Priority Data

Dec. 29, 2006  (KR) .................. 10-2006-0139039

(51) Int. Cl.
*C07D 233/00* (2006.01)
*C07D 249/00* (2006.01)
(52) U.S. Cl. .................. 548/262.2; 548/356.1
(58) Field of Classification Search ............. 548/262.2, 548/356.1
See application file for complete search history.

(56) References Cited

U.S. PATENT DOCUMENTS

2001/0047017 A1   11/2001   Komiyama et al.
2008/0287440 A1*  11/2008   Park et al. .............. 514/236.2

FOREIGN PATENT DOCUMENTS

| EP | 0 548 553 A1 | 6/1993 |
| EP | 0 659 751 A1 | 6/1995 |
| EP | 0 667 346 A2 | 8/1995 |
| WO | 2004/067537 A1 | 8/2004 |
| WO | WO2006/109933 | * 10/2006 |

OTHER PUBLICATIONS

European Search Report dated Jun. 17, 2010 in counterpart European Application No. 07851825.5.

* cited by examiner

*Primary Examiner* — Susannah Chung
(74) *Attorney, Agent, or Firm* — Sughrue Mion, PLLC

(57) ABSTRACT

The present invention relates to triazole derivatives, a method for the preparation thereof, and a pharmaceutical composition containing the same as an active ingredient. The inventive triazole derivaties have an excellent antifungal activity against various pathogens.

7 Claims, No Drawings

ANTIFUNGAL TRIAZOLE DERIVATIVES, METHOD FOR THE PREPARATION THEREOF AND PHARMACEUTICAL COMPOSITION CONTAINING SAME

CROSS REFERENCE TO RELATED APPLICATIONS

This application is a National Stage of International Application No. PCT/KR2007/006961 filed Dec. 28, 2007, claiming priority based on Korean Patent Application No. 10-2006-0139039, filed Dec. 29, 2006, the contents of which are incorporated herein by reference in their entirety.

FIELD OF THE INVENTION

The present invention relates to antifungal triazole derivatives, a method for the preparation thereof, and a pharmaceutical composition containing the same as an active ingredient.

BACKGROUND OF THE INVENTION

Patients having reduced immunity such as those undergoing chemical therapy for cancer, recovering from organ transplants, and suffering from AIDS are at a great risk of fungal infection, mostly by opportunistic pathogens such as *Candida* spp., *Aspergillus* spp. and *Cryptococcus neoformans*. The antifungals available in the market are not effective in such cases because of the problems of toxicity and narrow spectrum of activity.

There have been developed a number of antifungal compounds, e.g., orally administrable triazole derivatives represented by fluconazole (GB Patent No. 2099818), itraconazole (U.S. Pat. No. 4,267,179) and voriconazole (EP Patent No. 0440372). None of them, however, show inhibitory activity sufficiently effective for controlling the opportunistic fungi which cause fatal infection in such patients described above.

Many of the conventional antifungals have a structure comprising a triazole having an additional heterocyclic substituent. Disclosed are, for example, triazole derivatives having: a five-membered isoxazole (EP Patent No. 0241232); a triazolone moiety (EP Patent No. 0659751); and a pyrazole ring (Japanese Patent No. 3415865 and International Patent Publication No. WO 2001/79196).

However, the conventional derivatives disclosed in the above-mentioned patents are not completely satisfactory in treating severe fugal infection.

SUMMARY OF THE INVENTION

Accordingly, it is an object of the present invention to provide a novel triazole compound having antifungal activity against various pathogens, or an isomer or pharmaceutically acceptable salt thereof.

It is another object of the present invention to provide a method for preparing such compound.

It is a further object of the present invention to provide a pharmaceutical composition for treating fungal infection comprising said compound, or an isomer or pharmaceutically acceptable salt thereof as an active ingredient.

In accordance with one aspect of the present invention, there is provided a compound of formula (I), or an isomer or pharmaceutically acceptable salt thereof:

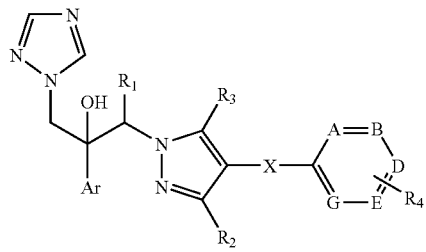

wherein,

Ar is phenyl substituted with at least one halogen or $C_1$-$C_4$ haloalkyl;

$R_1$ is hydrogen, fluorine or $C_1$-$C_4$ alkyl;

$R_2$, $R_3$ and $R_4$ are each independently hydrogen, halogen, $C_1$-$C_4$ alkyl, $C_1$-$C_4$ haloalkyl, $C_3$-$C_6$ cycloalkyl, $C_1$-$C_4$ alkoxy, nitro, cyano, amino, hydroxy, —$NR_5R_6$, —$CONR_5R_6$, —$CH_2$—CO—$R_5$, —$CH_2$—OCO—$R_5$, —CO—$R_5$, —$COOR_5$, —C(=$NR_5$)$NHR_7$, —C(=$NR_7$)$OR_7$, —$SO_ZR_7$, —$NR_5SO_2R_7$ or aryl $C_1$-$C_4$ alky, the aryl moiety being phenyl or naphtyl unsubstituted or substituted with at least one halogen, $C_1$-$C_4$ alkyl, $C_1$-$C_4$ haloalkyl, $C_1$-$C_4$ haloalkoxy, nitro, cyano, hydroxy or hydroxymethyl, wherein $R_4$ may represent two or more substituents independently selected from the above-mentioned substituents;

X is $C_1$-$C_4$ alkyl, $C_2$-$C_4$ alkenyl, or $C_2$-$C_4$ alkynyl unsubstituted or substituted with at least one halogen; O; $NR_2$; $CONR_2$;

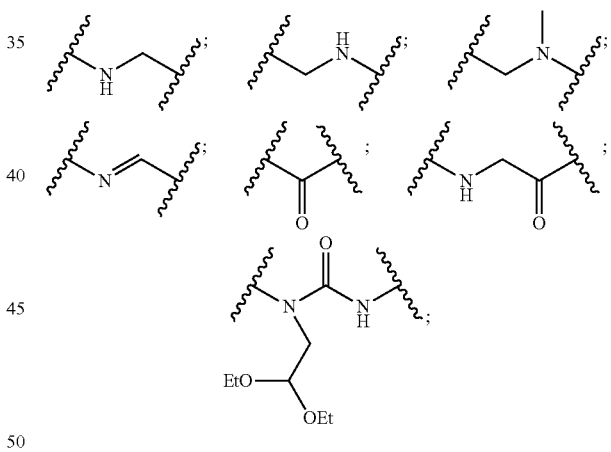

or Q-P unsaturated or substituted with O or $C_1$-$C_4$ *alky*;

Q being a linker, CO or $C_1$-$C_4$ alkyl, and P being a 5- to 7-membered heterocyclic ring containing at least one nitrogen or oxygen atom; and A, B, D, E and G are each independently nitrogen or carbon fused together to form a phenyl, pyridine, pyrimidine or triazine group, which is optionally fused with X to form a ring, in which $R_5$ is hydrogen, $C_1$-$C_4$ alkyl, $C_3$-$C_6$ cycloalkyl, —$COCF_3$, or the aryl $C_1$-$C_4$ alkyl defined for $R_2$;

$R_6$ is hydrogen, —$CONH_2$, —$COCH_3$, —CN, or —($C_1$-$C_4$ alkyl)-$NH_2$;

$R_7$ is $C_1$-$C_4$ alkyl, $C_3$-$C_6$ cylcoalkyl, or the aryl $C_1$-$C_4$ alkyl defined for $R_2$; and Z is 0, 1 or 2.

DETAILED DESCRIPTION OF THE INVENTION

Among the compounds of formula (I) of the present invention, preferred are those wherein:

Ar is phenyl substituted with at least one halogen or $C_1$-$C_4$ haloalkyl;

$R_1$ is hydrogen, fluorine or $C_1$-$C_4$ alkyl;

$R_2$, $R_3$ and $R_4$ are each independently hydrogen, halogen, $C_1$-$C_4$ alkyl, $C_1$-$C_4$ haloalkyl, $C_3$-$C_6$ cycloalkyl, $C_1$-$C_4$ alkoxy, nitro, cyano, amino or hydroxy, wherein $R_4$ may represent two or more substituents independently selected from the above-mentioned substituents;

X is $C_1$-$C_4$ alkyl or $C_1$-$C_4$ alkenyl unsubstituted or substituted with halogen; O; $NR_2$; $CONR_2$; $R_2$—O; $R_2$—$NR_3$; $R_2$—$OR_3$; $R_2$—CO—$R_3$; or Q-P unsubstituted or substituted with O or $C_1$-$C_4$ alkyl, Q being a linker, CO or $C_1$-$C_4$ alkyl, P being 5- to 7-membered heterocyclic ring containing at least one nitrogen or oxygen atom;

A, B, D, E and G are each independently nitrogen or carbon fused together to form a phenyl, pyridine, pyrimidine or triazine group, which is optionally fused with X to form a ring.

More preferred compounds of formula (I) according to the present invention are:

1) 1-(4-Chlorophenyl)-3-(1-((2R,3R)-3-(2,4-difluorophenyl)-3-hydroxy-4-(1H-1,2,4-triazol-1-yl)butan-2-yl)-1H-pyrazol-4-yl)imidazolidin-2-one;
2) 4-((E)-2-(1-((2R,3R)-3-(2,4-Difluorophenyl)-3-hydroxy-4-(1H-1,2,4-triazol-1-yl)butan-2-yl)-1H-pyrazol-4-yl)vinyl)benzonitrile;
3) (2R,3R)-2-(2,4-Difluorophenyl)-3-(4-(4-fluorobenzylamino)-1H-pyrazol-1-yl)-1-(1H-1,2,4-triazol-1-yl)butan-2-ol;
4) (2R,3R)-3-(4-(4-Chlorobenzylamino)-1H-pyrazol-1-yl)-2-(2,4-difluorophenyl)-1-(1H-1,2,4-triazol-1-yl)butan-2-ol;
5) (2R,3R)-3-(4-(4-Chlorophenylamino)methyl)-1H-pyrazol-1-yl)-2-(2,4-difluorophenyl)-1-(1H-1,2,4-triazol-1-yl)butan-2-ol;
6) (2R,3R)-3-(4-(4-Bromophenylamino)methyl)-1H-pyrazol-1-yl)-2-(2,4-difluorophenyl)-1-(1H-1,2,4-triazol-1-yl)butan-2-ol;
7) (2R,3R)-3-(4-(4-Nitrophenylamino)methyl)-1H-pyrazol-1-yl)-2-(2,4-difluorophenyl)-1-(1H-1,2,4-triazol-1-yl)butan-2-ol;
8) (2R,3R)-3-(4-(4-Chlorophenyl)(methyl)amino)methyl)-1H-pyrazol-1-yl)-2-(2,4-difluorophenyl)-1-(1H-1,2,4-triazol-1-yl)butan-2-ol;
9) (2R,3R)-3-(4-(4-Bromophenyl)(methyl)amino)methyl)-1H-pyrazol-1-yl)-2-(2,4-difluorophenyl)-1-(1H-1,2,4-triazol-1-yl)butan-2-ol;
10) (2R,3R,E)-2-(2,4-Difluorophenyl)-3-(4-(4-fluorobenzylideneamino)-1H-pyrazol-1-yl)-1-(1H-1,2,4-triazol-1-yl)butan-2-ol;
11) N-(1-((2R,3R)-3-(2,4-Difluorophenyl)-3-hydroxy-4-(1H-1,2,4-triazol-1-yl)butan-2-yl)-1H-pyrazol-4-yl)-4-fluorobenzamide;
12) 4-Chloro-N-(1-((2R,3R)-3-(2,4-difluorophenyl)-3-hydroxy-4-(1H-1,2,4-triazol-1-yl)butan-2-yl)-1H-pyrazol-4-yl)-benzamide;
13) 4-Chloro-N-(1-((2R,3R)-3-(2,4-difluorophenyl)-3-hydroxy-4-(1H-1,2,4-triazol-1-yl)butan-2-yl)-1H-pyrazol-4-yl)-N-methylbenzamide;
14) N-(4-Chlorophenyl)-1-((2R,3R)-3-(2,4-difluorophenyl)-3-hydroxy-4-(1H-1,2,4-triazol-1-yl)butan-2-yl)-N-methyl-1H-pyrazole-4-carboxamide;
15) (4-Chlorophenyl)-1-((2R,3R)-3-(2,4-difluorophenyl)-3-hydroxy-4-(1H-1,2,4-triazol-1-yl)butan-2-yl)-1H-pyrazol-4-yl)methanone;
16) 1-(4-Chlorophenyl)-2-(1-((2R,3R)-3-(2,4-difluorophenyl)-3-hydroxy-4-(1H-1,2,4-triazol-1-yl)butan-2-yl)-1H-pyrazol-4-ylamino)ethanone;
17) 1-(2,2-Diethoxyethyl)-1-(1-((2R,3R)-3-(2,4-difluorophenyl)-3-hydroxy-4-(1H-1,2,4-triazol-1-yl)butan-2-yl)-1H-pyrazol-4-yl)-3-(4-fluorophenyl)urea;
18) 3-(4-Chlorophenyl)-1-(2,2-diethoxyethyl)-1-(1-((2R,3R)-3-(2,4-difluorophenyl)-3-hydroxy-4-(1H-1,2,4-triazol-1-yl)butan-2-yl)-1H-pyrazol-4-yl)urea;
19) 1-(2,2-Diethoxyethyl)-1-(1-((2R,3R)-3-(2,4-difluorophenyl)-3-hydroxy-4-(1H-1,2,4-triazol-1-yl)butan-2-yl)-1H-pyrazol-4-yl)-3-(4-trifluoromethyl)phenyl)urea;
20) 3-(4-Text-butylphenyl)-1-(2,2-diethoxyethyl)-1-(1-((2R,3R)-3-(2,4-difluorophenyl)-3-hydroxy-4-(1H-1,2,4-triazol-1-yl)butan-2-yl)-1H-pyrazol-4-yl)urea;
21) 3-(2,4-Dichlorophenyl)-1-(2,2-diethoxyethyl)-1-(1-((2R,3R)-3-(2,4-difluorophenyl)-3-hydroxy-4-(1H-1,2,4-triazol-1-yl)butan-2-yl)-1H-pyrazol-4-yl)urea;
22) 1-(1-((2R,3R)-3-(2,4-Difluorophenyl)-3-hydroxy-4-(1H-1,2,4-triazol-1-yl)butan-2-yl)-1H-pyrazol-4-yl)-3-(4-fluorophenyl)-1H-imidazol-2(3H)-one;
23) 3-(4-Chlorophenyl)-1-(1-((2R,3R)-3-(2,4-difluorophenyl)-3-hydroxy-4-(1H-1,2,4-triazol-1-yl)butan-2-yl)-1H-pyrazol-4-yl)-1H-imidazole-2(3H)-one;
24) 1-(1-((2R,3R)-3-(2,4-Difluorophenyl)-3-hydroxy-4-(1H-1,2,4-triazol-1-yl)butan-2-yl)-1H-pyrazol-4-yl)-1H-3-(4-trifluoromethyl)phenyl) imidazole-2(3H)-one;
25) 3-(4-Tert-butylphenyl)-1-(1-((2R,3R)-3-(2,4-difluorophenyl)-3-hydroxy-4-(1H-1,2,4-triazol-1-yl)butan-2-yl)-1H-pyrazol-4-yl)-1H-imidazole-2(3H)-one;
26) 3-(2,4-Dichlorophenyl)-1-(1-((2R,3R)-3-(2,4-difluorophenyl)-3-hydroxy-4-(1H-1,2,4-triazol-1-yl)butan-2-yl)-1H-pyrazol-4-yl)-1H-imidazole-2(3H)-one;
27) (2R,3R)-2-(2,4-Difluorophenyl)-3-(4-((4-(4-fluorophenyl)piperazin-1-yl)methyl)-1H-pyrazol-1-yl)-1-(1H-1,2,4-triazol-1-yl)butan-2-ol;
28) (2R,3R)-2-(2,4-Difluorophenyl)-3-(4-((4-(4-nitrophenyl)piperazin-1-yl)methyl)-1H-pyrazol-1-yl)-1-(1H-1,2,4-triazol-1-yl)butan-2-ol;
29) 1-(4-Chlorophenyl)-4-((1-(2R,3R)-3-(2,4-difluorophenyl)-3-hydroxy-4-(1H-1,2,4-triazol-1-yl)butan-2-yl)-1H-pyrazol-4-yl)methyl)piperazin-2-one;
30) (1-(2R,3R)-2-(2,4-Difluorophenyl)-3-hydroxy-4-(1H-1,2,4-triazol-1-yl)butan-2-yl)-1H-pyrazol-4-yl)(4-(4-fluorophenyl)piperazin-1-yl)methanone;
31) (4-(4-Chlorophenyl)piperazin-1-yl)(1-(2R,3R)-2-(2,4-difluorophenyl)-3-hydroxy-4-(1H-1,2,4-triazol-1-yl)butan-2-yl)-1H-pyrazol-4-yl)methanone;
32) (1-(2R,3R)-2-(2,4-Difluorophenyl)-3-hydroxy-4-(1H-1,2,4-triazol-1-yl)butan-2-yl)-1H-pyrazol-4-yl)(4-(4-nitrophenyl)piperazin-1-yl)methanone;
33) (1-((2R,3R)-3-(2,4-Difluorophenyl)-3-hydroxy-4-(1H-1,2,4-triazol-1-yl)butan-2-yl)-N-(4-fluorophenyl)-5-methyl-1H-pyrazole-4-carboxamide;
34) N-(4-Chlorophenyl)-(1-((2R,3R)-3-(2,4-difluorophenyl)-3-hydroxy-4-(1H-1,2,4-triazol-1-yl)butan-2-yl)-5-methyl-1H-pyrazole-4-carboxamide;
35) N-(4-Chlorophenyl)-1-((2R,3R)-3-(2,4-difluorophenyl)-3-hydroxy-4-(1H-1,2,4-triazol-1-yl)butan-2-yl)-N,5-dimethyl-1H-pyrazole-4-carboxamide;
36) (4-(4-Chlorophenyl)piperazin-1-yl)(1-((2R,3R)-3-(2,4-difluorophenyl)-3-hydroxy-4-(1H-1,2,4-triazol-1-yl)butan-2-yl)-5-methyl-1H-pyrazol-4-yl)methanone;

37) (1-((2R,3R)-3-(2,4-Difluorophenyl)-3-hydroxy-4-(1H-1,2,4-triazol-1-yl)butan-2-yl)-5-methyl-1H-pyrazol-4-yl)(4-(4-nitrophenyl)piperazin-1-yl)methanone;

38) (2R,3R)-2-(2,4-Difluorophenyl)-3-(4-(4-fluorophenethyl)-1H-pyrazol-1-yl)-1-(1H-1,2,4-triazol-1-yl)butan-2-ol, 39) (2R,3R)-3-(4-(4-Chlorophenethyl)-1H-pyrazol-1-yl)-2-(2,4-difluorophenyl)-1-(1H-1,2,4-triazol-1-yl)butan-2-ol;

40) (2R,3R,E)-2-(2,4-Difluorophenyl)-3-(4-(4-fluorostyryl)-1H-pyrazol-1-yl)-1-(1H-1,2,4-triazol-1-yl)butan-2-ol, 41) (2R,3R,E)-3-(4-(4-Chlorostyryl)-1H-pyrazol-1-yl)-2-(2,4-difluorophenyl)-1-(1H-1,2,4-triazol-1-yl)butan-2-ol;

42) (2R,3R,E)-2-(2,4-Difluorophenyl)-3-(4-(4-nitrostyryl)-1H-pyrazol-1-yl)-1-(1H-1,2,4-triazol-1-yl)butan-2-ol;

43) (2R,3R,E)-2-(2,4-Difluorophenyl)-3-(4-(4-trifluoromethyl)styryl)-1H-pyrazol-1-yl)-1-(1H-1,2,4-triazol-1-yl)butan-2-ol;

44) (2R,3R,E)-3-(4-(3,4-Dichlorostyryl)-1H-pyrazol-1-yl)-2-(2,4-difluorophenyl)-1-(1H-1,2,4-triazol-1-yl)butan-2-ol;

45) (2R,3R)-2-(2,4-Difluorophenyl)-3-(4-(4-fluorophenyl)ethinyl)-1H-pyrazol-1-yl)-1-(1H-1,2,4-triazol-1-yl)butan-2-ol;

46) (2R,3R)-2-(2,4-Difluorophenyl)-3-(4-(2,4-difluorophenyl)ethinyl)-1H-pyrazol-1-yl)-1-(1H-1,2,4-triazol-1-yl)butan-2-ol;

47) (2R,3R)-2-(2,4-Difluorophenyl)-3-(4-(4-fluoro-3-methylphenyl)ethinyl)-1H-pyrazol-1-yl)-1-(1H-1,2,4-triazol-1-yl)butan-2-ol, 48) 4-((1-(2R,3R)-3-(2,4-Difluorophenyl)-3-hydroxy-(4-(1H-1,2,4-triazol-1-yl)butan-2-yl)-1H-pyrazol-4-yl)ethinyl)benzonitrile;

49) (2R,3R)-2-(2,4-Difluorophenyl)-3-(4-(4-fluorobenzyl)-1H-pyrazol-1-yl)-1-(1H-1,2,4-triazol-1-yl)butan-2-ol;

50) (2R,3R)-3-(4-(4-Chlorobenzyl)-2-(2,4-difluorophenyl)-1H-pyrazol-1-yl)-1-(1H-1,2,4-triazol-1-yl)butan-2-ol;

51) (2R,3R,E)-2-(2,4-Difluorophenyl)-3-(4-(2-(pyridin-2-yl)vinyl)-1H-pyrazol-1-yl)-1-(1H-1,2,4-triazol-1-yl)butan-2-ol;

52) (2R,3R,E)-2-(2,4-Difluorophenyl)-3-(4-(2-(pyridin-3-yl)vinyl)-1H-pyrazol-1-yl)-1-(1H-1,2,4-triazol-1-yl)butan-2-ol;

53) (2R,3R,E)-2-(2,4-Difluorophenyl)-3-(4-(2-(pyrazin-2-yl)vinyl)-1H-pyrazol-1-yl)-1-(1H-1,2,4-triazol-1-yl)butan-2-ol;

54) (2R,3R,E)-2-(2,4-Difluorophenyl)-3-(4-(2-(6-methylpyridin-2-yl)vinyl)-1H-pyrazol-1-yl)-1-(1H-1,2,4-triazol-1-yl)butan-2-ol;

55) (2R,3R,E)-2-(2,4-Difluorophenyl)-3-(4-(2-(5-nitropyridin-2-yl)vinyl)-1H-pyrazol-1-yl)-1-(1H-1,2,4-triazol-1-yl)butan-2-ol, 56) (2R,3R,E)-2-(2,4-Difluorophenyl)-3-(4-(2-(3-methyl-5-nitropyridin-2-yl)vinyl)-1H-pyrazol-1-yl)-1-(1H-1,2,4-triazol-1-yl)butan-2-ol;

57) (2R,3R,E)-2-(2,4-Difluorophenyl)-3-(4-(2-(6-nitropyridin-3-yl)vinyl)-1H-pyrazol-1-yl)-1-(1H-1,2,4-triazol-1-yl)butan-2-ol, 58) 5-(((E)-2-(1-((2R,3R)-3-(2,4-Difluorophenyl)-3-hydroxy-4-(1H-1,2,4-triazol-1-yl)butan-2-yl)-1H-pyrazol-4-yl)vinyl)nicotinonitrile;

59) (2R,3R,E)-3-(4-(2-(5-Chloropyridin-2-yl)vinyl)-1H-pyrazol-1-yl)-2-(2,4-difluorophenyl)-1-(1H-1,2,4-triazol-1-yl)butan-2-ol;

60) (2R,3R)-2-(2,4-Difluorophenyl)-3-(4-(pyridin-2-ylethinyl)-1H-pyrazol-1-yl)-1-(1H-1,2,4-triazol-1-yl)butan-2-ol, 61) (2R,3R)-2-(2,4-Difluorophenyl)-3-(4-(pyridin-3-ylethinyl)-1H-pyrazol-1-yl)-1-(1H-1,2,4-triazol-1-yl)butan-2-ol;

62) (2R,3R)-2-(2,4-Difluorophenyl)-3-(4-(5-nitropyridin-2-ylethinyl)-1H-pyrazol-1-yl)-1-(1H-1,2,4-triazol-1-yl)butan-2-ol;

63) (2R,3R)-2-(2,4-Difluorophenyl)-3-(4-(6-nitropyridin-3-ylethinyl)-1H-pyrazol-1-yl)-1-(1H-1,2,4-triazol-1-yl)butan-2-ol;

64) (2R,3R)-2-(2,4-Difluorophenyl)-3-(4-(3-methyl-5-nitropyridin-2-ylethinyl)-1H-pyrazol-1-yl)-1-(1H-1,2,4-triazol-1-yl)butan-2-ol;

65) (2R,3R)-3-(4-((5-Chloropyridin-2-yl)ethinyl)-1H-pyrazol-1-yl)-2-(2,4-difluorophenyl)-1-(1H-1,2,4-triazol-1-yl)butan-2-ol;

66) (2R,3R)-2-(2,4-Difluorophenyl)-3-(4-(quinolin-4-yl)-1H-pyrazol-1-yl)-1-(1H-1,2,4-triazol-1-yl)butan-2-ol;

67) (2R,3R)-2-(2,4-Difluorophenyl)-3-(4-(quinoxalin-3-yl)-1H-pyrazol-1-yl)-1-(1H-1,2,4-triazol-1-yl)butan-2-ol; and 68) (2R,3R)-3-(4-(Benzofuran-2-yl)-1H-pyrazol-1-yl)-2-(2,4-difluorophenyl)-1-(1H-1,2,4-triazol-1-yl)butan-2-ol.

Unless otherwise specified, the term "halogen" or "halo", as used herein, represents a halogen atom such as fluorine, chlorine, bromine, and iodine.

Unless otherwise specified, the term "alkyl", as used herein, means a straight or branched saturated hydrocarbon radical having 1 to 4 carbon atoms, examples of which include methyl, ethyl, propyl, isopropyl, butyl, isobutyl, sec-butyl, and tent-butyl.

Unless otherwise specified, the term "haloalkyl", as used herein, means a radical in which one or more hydrogen substituents of an alkyl group (as defined above) are replaced with one or more identical or different halogens, examples of which include trifluoromethyl, trichloromethyl, fluoromethyl, chloromethyl, bromomethyl, iodomethyl, difluoromethyl, dichloromethyl, 2-chloroethyl, 2,2-dichloroethyl, 2,2,2-trichloroethyl, pentachloroethyl, 2-fluoroethyl, 2,2-difluoroethyl, 2,2,2-trifluoroethyl, pentafluoroethyl, 3-chloropropyl, 3,3-dichloropropyl, 3,3,3-trichloropropyl, 2,2,3,3,3-pentachloropropyl, 3-fluoropropyl, 3,3-difluoropropyl, 3,3,3-trifluoropropyl, 2,2,3,3-tetrafluoropropyl, 2,2,3,3,3-pentafluoropropyl, heptafluoropropyl, 4-chlorobutyl, 4-fluorobutyl, 4-iodobutyl, and 4-bromobutyl.

As used herein, the term "cycloalkyl", unless otherwise specified, means a saturated cyclic hydrocarbon radical having 3 to 6 carbon atoms, exemplified by cyclopropyl, cyclobutyl, cyclopentyl, or cyclohexyl.

As used herein, the term "alkoxy", unless otherwise specified, means O-alkyl (wherein the alkyl moiety is as defined above), examples of which are methoxy, ethoxy, propoxy, isopropoxy, butoxy, isobutoxy, sec-butoxy, and tert-butoxy.

As used herein, the term "haloalkoxy", unless otherwise specified, means an alkoxy radical in which one or more hydrogen substituents are substituted with one or more identical or different halogen atoms. Examples of "haloalkoxy" as used herein include trifluoromethoxy, fluoromethoxy, 2-chloroethoxy, 2-fluoroethoxy, 2,2-difluoroethoxy, 2-iodoethoxy, 2,2-difluoroethoxy, 2,2,2-trifluoroethoxy, pentafluoroethoxy, 3-fluoropropoxy, 3-chloropropoxy, 2,2,3,3-tetrafluoropropoxy, 2,2,3,3,3-pentafluoropropoxy, heptafluoropropoxy, 4-fluorobutoxy, and 4-chlorobutoxy, but is not limited thereto.

The term "aryl $C_1$-$C_4$ alkyl", as used herein, means a substituent in which at least one of the hydrogen atoms of $C_1$-$C_4$ alkyl is substituted with an aryl group. The term "aryl" is an aromatic hydrocarbon radical such as phenyl or naphthyl, unless otherwise indicated.

The compound of formula (I) according to the present invention contains chiral centers at the C2 and C3 positions. Namely, the inventive compound of formula (I) have an optically pure (2R,3R)-configuration at the C2 and C3 position. Therefore, it should be understood that the compound of the present invention includes all possible stereoisomers, unless otherwise specified.

The compound of formula (I) of the present invention may be in the form of a pharmaceutically acceptable salt derived using an inorganic or organic acid known in the art relating to the preparation of conventional antifungals. Representative examples of the acids used in the present invention include hydrochloric acid, nitric acid, methansulfonic acid and oxalic acid.

In accordance with another embodiment, there is provided a method for preparing the compound of formula (I) comprising the steps of: allowing a compound of formula (II) to react with a compound of formula (III) in the presence of a base to obtain a compound of formula (IV); and converting the compound of formula (IV) to a compound of formula (I), or an isomer or pharmaceutically acceptable salt thereof according to any of the methods known in the art:

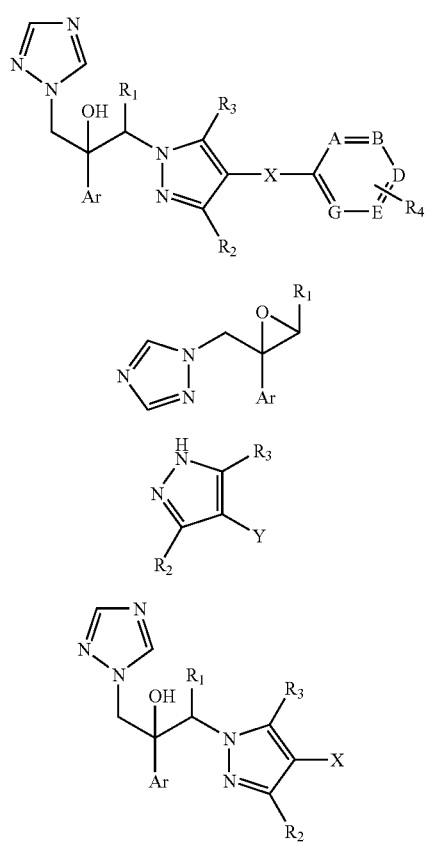

wherein, Ar, A, B, D, E, G, X, $R_1$, $R_2$, $R_3$ and $R_4$ have the same meanings as defined above; and Y is —$NO_2$, —$B(OH)_2$, —$B(OC(CH_3)_2)_2$, —CHO, Cl, Br, I, —$CH_2Cl$, —$CH_2Br$, —$CO_2H$, —$NH_2$, —COCl, —CH=$CH_2$, or —C≡CH.

The inventive method for preparing the compound of formula (I) is shown in Reaction Scheme A.

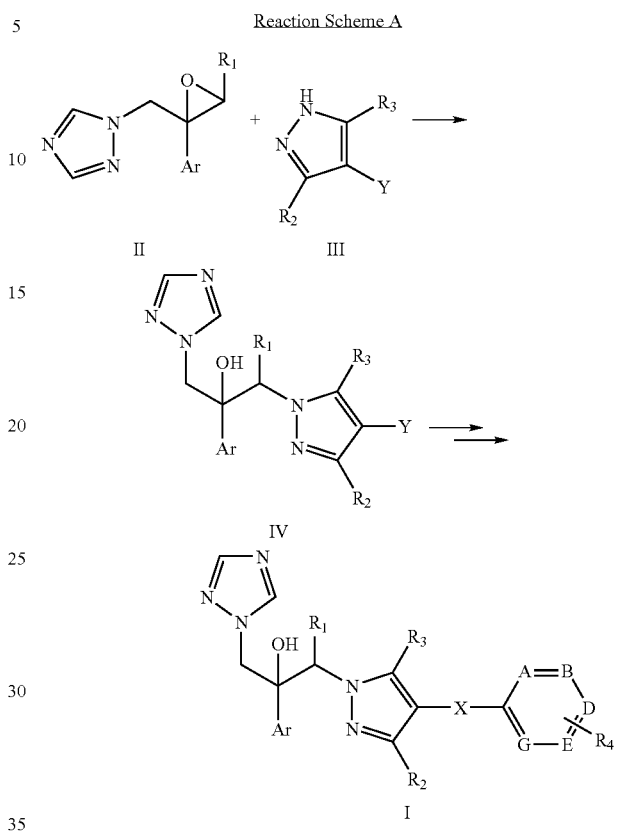

Reaction Scheme A wherein, Ar, A, B, D, E, G, X, $R_1$, $R_2$, $R_3$ and $R_4$ have the same meanings as defined above; and Y is —$NO_2$, —$B(OH)_2$, —$B(OC(CH_3)_2)_2$, —CHO, Cl, Br, I, —$CH_2Cl$, —$CH_2Br$, —$CO_2H$, —$NH_2$, —COCl, —CH=$CH_2$, or —C≡CH.

The compound of formula (II) used as a starting material in Reaction Scheme A may be prepared by a conventional method (see *Chem. Pharm. Bull.* Tasaka et al., 1993, 41(6), 1035-1042), and the compound of formula (III) is commercially available, or may be prepared in accordance with any of the conventional methods.

The compound of formula (IV) may be prepared by reacting the compound of formula (II) with the compound of formula (III) in accordance with the conventional method (see, *J. Org. Chem.* Erdélyi et al., 2001, 66(12), 4165-4169; *Tetrahedron*, Haley et al., 2004, 60(5), 1215-1223; *Org. Lett.* Sa et al., 2003, 5(17), 3119-3121), and depending on the substituent Y of formula (III), an appropriate method may be used.

The reaction according to the present invention may be carried out in a polar organic solvent which is preferably methanol, acetonitrile, dimethoxyethane, dimethylformamide, dimethylsulfoxide or tetrahydrofuran, while the base used in the present invention may be an inorganic base such as sodium hydride (NaH), potassium carbonate ($K_2CO_3$) or sodium methoxide (NaOMe), or an organic base such as triethylamine or 1,8-diazabicyclo[5,4,0]undec-7-ene (DBU).

The reaction to prepare the compound of formula (IV) may be carried out at a temperature in the range of 0 to 200° C., preferably at a temperature in the range of 30 to 200° C., for 2 minutes to 24 hours with stirring.

The compound of formula (I) may be obtained by converting the compound of formula (IV) thus obtained according to a conventional method (see *Tetrahedron Lett*. Arya et al., 1995, 36(25), 4369-4372). Alternatively, for example, the compound of formula (I) may be synthesized by using the reported method [*J. Hetero. Chem*. Miller et al., 1993, 30, 755-763; *Synthesis*, Kuang et al., 2005, 1319-1325] as shown in Reaction Scheme B:

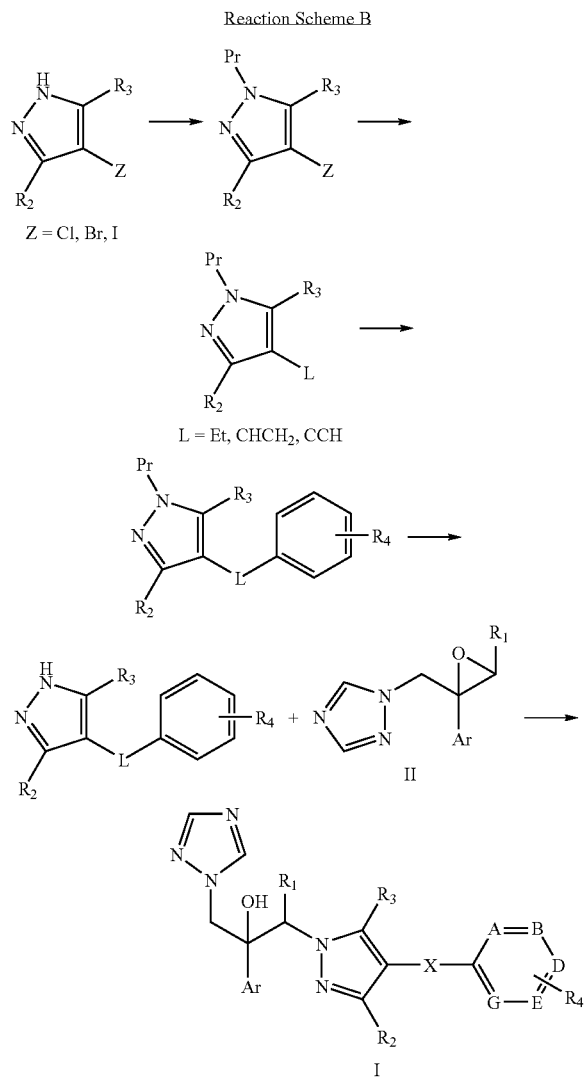

wherein,

Ar, A, B, D, E, G, X, $R_1$, $R_2$, $R_3$ and $R_4$ have the same meanings as defined above, and Pr is a protecting group for the NH moiety of the pyrazole ring selected from the group consisting of benzyl, para-methoxy benzyl, trityl, methoxy methyl, 2-methoxyetheoxy methyl, 2-(trimethylsilyl)ethoxymethyl, tetrahydropyranyl, or 1-ethoxyethyl.

The compound of formula (I), or an isomer or pharmaceutically acceptable salt thereof according to the present invention has excellent antifungal activity against various pathogenic fungi. Representative examples of the fungi include *Candida* spp., *Aspergillus* spp., *Cryptococcus neoformans*, *Trichophyton* spp., *Fusarium* spp., *Scedosporium* spp., *Absidia* spp., *Blastomyces* spp., and *Rhizopus* spp.

In accordance with further aspect of the present invention, there is provided a pharmaceutical composition for treating fungal infection comprising the compound of formula (I), or an isomer or pharmaceutically acceptable salt thereof.

The pharmaceutically acceptable composition may be formulated with the compound of the present invention, or an isomer or pharmaceutically acceptable salt thereof in combination with an inert pharmaceutical vehicle or diluent for oral, parenteral or topical administration into various dosage forms using conventional methods.

The composition for oral administration may take various forms such as tablet or capsules, such formulations may comprise the active ingredient together with diluting agents (e.g., lactose, dextrose, sucrose, mannitol, sorbitol, cellulose and/or glycine), and lubricants (e.g., silica, talc, stearic acid and a magnesium or calsium salt thereof and/or polyethyleneglycol). Further, these tablets may comprise binding agents such as magnesium aluminum silicate, starch paste, gelatin, tragacanth, methylcellulose, sodium carboxymethylcellulose and/or polyvinylpyrrolidine, and may further comprise disintergrants such as starch, agarose, alginate or a sodium salt thereof or an effervescent mixture and/or an absorbing, colouring, flavouring, and sweetening agents.

Further, the inventive pharmaceutical composition may take forms of preferably injections further comprising aqueous isotonic solutions or suspensions when formulated for parenteral administration.

The dosage of the active ingredient may be adjusted in light of various relevant factors including the condition to be treated, the severity of the patient's symptoms, the route of administration, sex and opinion of doctor. The therapeutically effective dose of the compound of the present invention can be readily determined by those who are skilled in the art. The inventive compound can be administered orally or parenterally in an effective amount ranging from about 0.05 to 200 mg/kg (body weight), preferably 0.05 to 100 mg/kg (body weight) per day in case of a mammal including a human being in a single dose or in divided doses.

The following Examples are intended to further illustrate the present invention without limiting its scope.

EXAMPLE 1

1-(4-Chlorophenyl)-3-(1-(((2R,3R)-3-(2,4-difluorophenyl)-3-hydroxy-4-(1H-1,2,4-triazol-1-yl)butan-2-yl)-1H-pyrazol-4-yl)imidazolidin-2-one

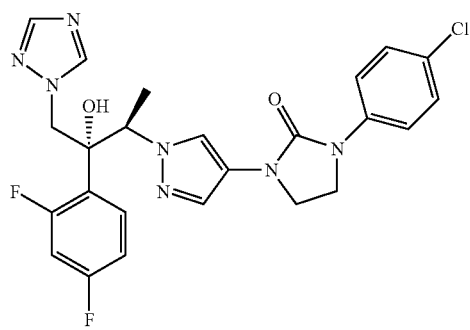

Step 1: (2R,3R)-2-(2,4-Difluorophenyl)-3-(4-nitro-1H-pyrazol-1-yl)-1-(1H-1,2,4-triazol-1-yl)butan-2-ol 4-Nitropyrazole (0.5 g, 4.42 mmol) and 1-(((2R,3S)-2-(2,4-difluorophenyl)-3-methyloxiran-2-yl)methyl)-1H-1,2,4- triazol (0.93 g, 3.68 mmol) were suspended in N,N-dimethylformamide (20 mL), and anhydrous potassium carbonate (0.61 g, 4.44 mmol) was added thereto, followed by heating at 180° C. for 5 minutes by microwave irradiation while stirring. After completion of the reaction, the resulting mixture was extracted with ethyl acetate (200 mL), and the extract was washed successively with saturated ammonium chloride (200 mL) and brine (200 mL). The organic layer was dried over anhydrous magnesium sulfate and concentrated by evaporation under a reduced pressure. The resulting residue was purified by silica gel chromatography to obtain the title compound (1.0 g, yield 75%).

$^1$H NMR (CDCl$_3$): δ 8.53 (s, 1H), 8.11 (s, 1H), 7.77 (s, 1H), 7.76 (s, 1H), 7.45 (m, 1H), 6.80 (m, 2H), 5.11 (q, 1H), 4.97 (d, 1H, J=14.3 Hz), 3.67 (d, 1H, J=14.3 Hz), 1.37 (d, 3H, J=7.1 Hz).

Step 2: (2R,3R)-3-(4-Amino-1H-pyrazol-1-yl)-2-(2,4-difluorophenyl)-1-(1H-1,2,4-triazol-1-yl)butan-2-ol (2R,3R)-2-(2,4-difluorophenyl)-3-(4-nitro-1H-pyrazol-1-yl)-1-(1H-1,2,4-triazol-1-yl)butan-2-ol obtained in Step 1 (0.2 g, 0.55 mmol) was dissolved in methanol (15 mL) and 5% palladium on charcoal (5% Pd/C, 0.02 g) was added thereto, and the resulting mixture was stirred for 4 hours under a hydrogen atmosphere. The reaction solution was filtered through celite and the filtrate was concentrated by evaporation under a reduced pressure to obtain the title compound (0.16 g, yield 87%).

$^1$H NMR (CDCl$_3$): δ 7.86 (s, 1H), 7.65 (s, 1H), 7.47 (m, 1H), 7.30 (s, 1H), 7.26 (s, 1H), 6.78 (m, 2H), 5.88 (s, 1H), 4.91-4.78 (m, 2H), 3.63 (d, 1H, J=14.3 Hz), 1.27 (d, 3H, J=7.0 Hz).

Step 3: (2R,3R)-3-(4-(2,2-Diethoxyethylamino)-1H-pyrazol-1-yl)-2-(2,4-difluorophenyl)-1-(1H-1,2,4-triazol-1-yl)butan-2-ol (2R,3R)-3-(4-amino-1H-pyrazol-1-yl)-2-(2,4-difluorophenyl)-1-(1H-1,2,4-triazol-1-yl)butan-2-ol obtained in Step 2 (0.12 g, 0.35 mmol) was dissolved in N,N-dimethylformamide (2 mL) and triethylamine (0.058 g, 0.42 mmol) was slowly added thereto. The mixture was stirred at room temperature for 30 minutes, and bromoacetaldehyde diethyl acetal (0.065 mL, 0.42 mmol) was added thereto, followed by stirring at 80° C. for 4 hours. The reaction was terminated by adding ice water (0.1 mL) thereto. The resulting residue was extracted with ethyl acetate (20 mL), and the extract was washed successively with saturated ammonium chloride (20 mL) and brine (20 mL). The organic layer was dried over anhydrous magnesium sulfate and concentrated by evaporation under a reduced pressure. The resulting residue was purified by silica gel chromatography to obtain the title compound (0.071 g, yield 44%).

$^1$H NMR (CDCl$_3$): δ 7.84 (s, 1H), 7.63 (s, 1H), 7.45 (m, 1H), 7.25 (s, 1H), 7.24 (s, 1H), 6.76 (m, 2H), 5.83 (s, 1H), 5.28 (s, 1H), 4.85 (q, 1H), 4.79 (d, 1H, J=14.7 Hz), 4.68 (t, 1H, J=5.5 Hz), 3.74 (m, 2H), 3.57 (m, 3H), 3.11 (d, 2H, J=5.5 Hz), 1.24 (m, 9H).

Step 4: 3-(4-Chlorophenyl)-1-(2,2-diethoxyethyl)-1-(1-((2R,3R)-3-(2,4-difluorophenyl)-3-hydroxy-4-(1H-1,2,4-triazol-1-yl)butan-2-yl)-1H-pyrazol-4-yl)urea [see Chem. Pharm. Bull. Ichikawa et al., 2000, 48(12), 1947-1953]

(2R,3R)-3-(4-(2,2-diethoxyethylamino)-1H-pyrazol-1-yl)-2-(2,4-difluorophenyl)-1-(1H-1,2,4-triazol-1-yl)butan-2-ol thus obtained in Step 3 (0.06 g, 0.14 mmol) was dissolved in N,N-dimethylformamide (1 mL) and 4-chlorophenylisocyanate (0.017 mL, 0.14 mmol) was added thereto. The mixture was stirred at room temperature for 12 hours. The resulting mixture was extracted with ethyl acetate (10 mL), and the extract was washed successively with saturated ammonium chloride (10 mL) and brine (10 mL). The organic layer was dried over anhydrous magnesium sulfate and concentrated by evaporation under a reduced pressure. The resulting residue was purified by silica gel chromatography to obtain the title compound (0.076 g, yield 95%).

$^1$H NMR (CDCl$_3$): δ 8.15 (s, 1H), 8.12 (s, 1H), 7.58 (m, 2H), 7.55 (s, 1H), 7.45 (s, 1H), 7.41 (m, 2H), 7.15 (m, 1H), 6.65 (m, 2H), 5.74 (s, 1H), 4.91 (q, 1H), 4.79 (d, 1H, J=14.7 Hz), 4.78 (t, 1H, J=5.5 Hz), 4.30 (m, 2H), 3.46 (m, 3H), 3.31 (d, 2H, J=5.5 Hz), 1.31 (m, 9H).

Step 5: 3-(4-Chlorophenyl)-1-(1-((2R,3R)-3-(2,4-difluorophenyl)-3-hydroxy-4-(1H-1,2,4-triazol-1-yl)butan-2-yl)-1H-pyrazol-4-yl)-1H-imidazol-2(3H)-one 3-(4-Chlorophenyl)-1-(2,2-diethoxyethyl)-1-(1-((2R,3R)-3-(2,4-difluorophenyl)-3-hydroxy-4-(1H-1,2,4-triazol-1-yl)butan-2-yl)-1H-pyrazol-4-yl)urea obtained in Step 4 (0.07 g, 0.12 mmol) was dissolved in methanol (2 mL) and 1N-HCl (2 mL) was added thereto. The mixture was refluxed for 2 hours, and neutralized using aqueous sodium hydrogen carbonate. The resulting mixture was extracted with ethyl acetate (10 mL), and the extract was washed successively with distilled water (10 mL) and brine (10 mL). The organic layer was dried over anhydrous magnesium sulfate and concentrated by evaporation under a reduced pressure. The resulting residue was purified by silica gel chromatography to obtain the title compound (0.056 g, yield 95%).

$^1$H NMR (CDCl$_3$): δ 8.28 (s, 1H), 7.80 (s, 1H), 7.76 (s, 1H), 7.68 (s, 1H), 7.58 (d, 2H), 7.51 (m, 1H), 7.41 (d, 2H), 6.79 (m, 2H), 6.72 (m, 2H), 5.59 (s, 1H), 5.05 (q, 1H), 4.89 (d, 1H, J=14.3 Hz), 3.65 (d, 1H, J=14.3 Hz), 1.35 (d, 3H, J=6.9 Hz).

Step 6: 1-(4-Chlorophenyl)-3-(1-((2R,3R)-3-(2,4-difluorophenyl)-3-hydroxy-4-(1H-1,2,4-triazol-1-yl)butan-2-yl)-1H-pyrazol-4-yl)imidazolidin-2-one [see Chem. Pharm. Bull. Ichikawa et al., 2000, 48(12), 1935-1946; Chem. Pharm. Bull. Kitazaki et al., 1999, 47(3), 351-359]

3-(4-Chlorophenyl)-1-(1-((2R,3R)-3-(2,4-difluorophenyl)-3-hydroxy-4-(1H-1,2,4-triazol-1-yl)butan-2-yl)-1H-pyrazol-4-yl)-1H-imidazol-2(3H)-one obtained in Step 5 (0.026 g, 0.051 mmol) was dissolved in acetic acid (1 mL), and 5% palladium on charcoal (5% Pd/C, 0.01 g) was added thereto, and the resulting mixture was stirred for 3 hours under a hydrogen atmosphere. The reaction mixture was filtered through celite and the filtrate was concentrated by evaporation under a reduced pressure to obtain the title compound (0.016 g, yield 62%).

$^1$H-NMR (CDCl$_3$): δ 8.09 (s, 1H), 7.81 (s, 1H), 7.65 (s, 1H), 7.60-7.54 (m, 3H), 7.47 (m, 1H), 7.33 (d, 2H), 6.80 (m, 2H), 5.69 (s, 1H), 5.01 (q, 1H), 4.86 (d, 1H, J=14.6 Hz), 4.01 (t, 2H), 3.91 (t, 2H), 3.61 (d, 1H, J=14.2 Hz), 1.33 (d, 3H, J=7.0 Hz).

EXAMPLE 2

4-((E)-2-(1-((2R,3R)-3-(2,4-Difluorophenyl)-3-hydroxy-4-(1H-1,2,4-triazol-1-yl)butan-2-yl)-1H-pyrazol-4-yl)vinyl)benzonitrile

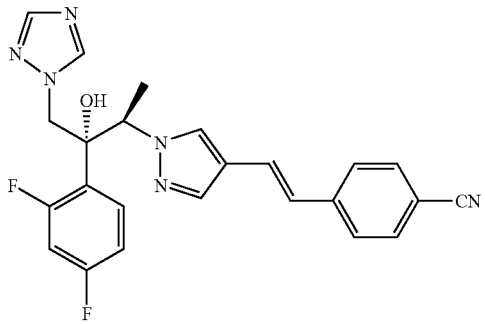

Step 1: 1-(1-Ethoxyethyl)-4-iodo-1H-pyrazole

4-Iodo-1H-pyrazole (3.0 g) was suspended in benzene (150 mL) and the suspension was heated while stirring. Ethyl vinyl ether (4.4 mL) was added thereto, concentrated HCl was added dropwise thereto, and the resulting mixture was stirred at 60° C. for 3 hours. After completion of the reaction, the resulting mixture was concentrated by evaporation under a reduced pressure, and the residue was neutralized using aqueous saturated sodium hydrogen carbonate (10 mL). The resulting mixture was extracted with ethyl acetate (50 mL) and the extract was washed successively with distilled water (100 mL). The organic layer was dried over anhydrous magnesium sulfate and concentrated by evaporation under a reduced pressure. The resulting residue was purified by silica gel chromatography to obtain the title compound as a transparent yellow liquid (3.0 g, yield 73%).

$^1$H NMR (CDCl$_3$): δ 7.54 (s, 1H), 7.41 (s, 1H), 5.40 (q, 1H, J=6.0 Hz), 3.38-3.18 (m, 2H), 1.54 (d, 3H, J=6.0 Hz), 1.05 (t, 3H, J=7.1 Hz).

Step 2: 4-((E)-2-(1-(1-Ethoxyethyl)-1H-pyrazol-4-yl) vinyl)benzonitrile 1-(1-Ethoxyethyl)-4-iodo-1H-pyrazole obtained in Step 1 (162.0 mg) was suspended in N,N-methylformamide (5.0 mL), and added thereto were 4-vinylbenzonitrile (157.3 mg), tetrabutylamonuim bromide (19.6 mg), paladium acetate (41.0 mg) and potassium carbonate (210.4 mg). The mixture was stirred at room temperature for 10 minutes, and subjected to microwave irradiation at 140° C. for 20 minutes. After completion of the reaction, the resulting mixture was filtered through silica gel, and extracted with ethyl acetate (15 mL). The extract was washed successively with saturated ammonium chloride (15 mL) and brine (15 mL). The organic layer was dried over anhydrous magnesium sulfate and concentrated by evaporation under a reduced pressure. The resulting residue was purified by silica gel chromatography to obtain the title compound (0.11 g, yield 61%).

$^1$H NMR (CDCl$_3$): δ 7.73 (s, 1H), 7.72 (s, 1H), 7.61 (d, 2H, J=8.3 Hz), 7.50 (d, 2H, J=8.3 Hz), 7.08 (d, 1H, J=16.4 Hz), 6.84 (d, 1H, J=16.4 Hz), 5.52 (q, 1H, J=6.0 Hz), 3.52-3.33 (m, 2H), 1.68 (d, 31-1, J=6.0 Hz), 1.17 (t, 3H, J=7.0 Hz).

Step 3: 4-((E)-2-(1H-Pyrazol-4-yl)vinyl)benzonitrile 4-((E)-2-(1-(1-ethoxyethyl)-1H-pyrazol-4-yl)vinyl)benzonitrile in obtained in Step 2 (66.1 mg) was suspended in 1N-HCl (3 mL) and tetrahydrofuran (6 mL). The suspension was stirred at room temperature for 10 minutes, and reacted by microwave irradiation at 80° C. for 30 minutes. After completion of the reaction, the resulting mixture was extracted with ethyl acetate (10 mL) and the extract was neutralized using saturated sodium hydrogen carbonate (5 mL), followed by washing with distilled water (10 mL) and brine (10 mL). The organic layer was dried over anhydrous magnesium sulfate and concentrated by evaporation under a reduced pressure. The resulting residue was purified by silica gel chromatography to obtain the title compound (0.045 g, yield 93%).

$^1$H NMR (CDCl$_3$): δ 7.81 (s, 2H), 7.68-7.60 (m, 2H), 7.55-7.50 (m, 2H), 7.12 (d, 2H, J=16.4 Hz), 6.88 (d, 1H, J=16.4 Hz).

Step 4: 4-((E)-2-(1-((2R,3R)-3-(2,4-Difluorophenyl)-3-hydroxy-4-(1H-1,2,4-triazol-1-yl)butan-2-yl)-1H-pyrazol-4-yl)vinyl)benzonitrile 1-(((2R,3S)-2-(2,4-difluorophenyl)-3-methyl oxiran-2-yl) methyl)-1H-1,2,4-triazol obtained in step 3 (55.9 mg) was suspended in N,N-dimethylformamide (1.6 mL), and calcium carbonate (41.9 mg) and 4-((E)-2-(1H-pyrazol-4-yl)vinyl) benzonitrile (39.5 mg) were added thereto. The mixture was stirred at room temperature for 20 minutes under an argon atmosphere, and reacted by microwave irradiation at 180° C. for 15 minutes. After completion of the reaction, the resulting mixture was extracted with ethyl acetate (10 mL) and the extract was washed successively with saturated amonium-chloride (10 mL) and brine (10 mL). The organic layer was dried over anhydrous magnesium sulfate and concentrated by evaporation under a reduced pressure. The resulting residue was purified by silica gel chromatography to obtain the title compound (0.039 g, yield 43.5%).

$^1$H NMR (CDCl$_3$): δ 7.88 (s, 1H), 7.85 (s, 1H), 7.79 (s, 1H), 7.70 (s, 1H), 7.63 (s, 1H), 7.61 (s, 1H), 7.53-7.49 (m, 3H), 7.10 (d, 1H, J=16.4 Hz), 6.88 (d, 1H, J=16.4 Hz), 6.83-6.77 (m, 2H), 5.70 (bs, 1H), 5.07 (q, 1H, J=7.0 Hz), 4.89 (d, 1H, J=14.0 Hz), 3.66 (d, 1H, J=14.2 Hz), 1.35 (d, 3H, J=7.0 Hz).

EXAMPLES 3 to 32

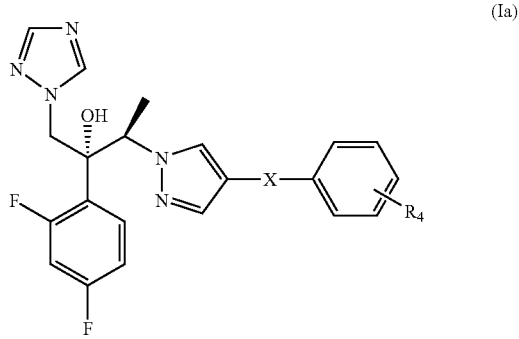

(Ia)

Procedures similar to that of Example 1 were performed to synthesize various compounds represented by formula (Ia), X and R$_4$ being listed in Table 1:

TABLE 1

| Examples | X | R₄ | ¹H-NMR (300 MHz, CDCl₃) δ |
|---|---|---|---|
| 3 | —NH— (CH) | 4-F | 7.87(s, 1 H), 7.69(s, 1 H), 7.43-7.42(m, 1 H), 7.28(s, 1 H), 7.23-7.22(m, 3 H), 7.18(s, 1 H), 7.02(s, 1 H), 6.79-6.72(m, 2 H), 4.83-4.77(q, 1 H), 4.70(d, 1 H), 3.41(d, 1 H), 1.22(d, 3 H). |
| 4 | —NH— (CH) | 4-Cl | 7.82(s, 1 H), 7.68(s, 1 H), 7.44-7.42(m, 1 H), 7.28(s, 1 H), 7.24-7.22(m, 3 H), 7.18(s, 1 H), 7.02(s, 1 H), 6.79-6.72(m, 2 H), 4.83-4.77(q, 1 H), 4.70(d, 1 H), 3.41(d, 1 H), 1.22(d, 3 H). |
| 5 | —CH₂—NH— | 4-Cl | 7.83(s, 1 H), 7.66(s, 2 H), 7.57(s, 1 H), 7.53-7.45(m, 1 H), 7.14(d, 2 H), 6.82-6.76(q, 2 H), 6.60(d, 2 H), 5.04-4.97(q, 1 H), 4.80(d, 1 H), 4.21(s, 2 H), 3.61(d, 1 H), 1.31(d, 3 H). |
| 6 | —CH₂—NH— | 4-Br | 7.97(s, 1 H), 7.81(s, 1 H), 7.43(s, 1 H), 7.38(s, 1 H), 7.28-7.25(d, 2 H), 6.98-6.96(m, 1 H), 6.83-6.76(m, 2 H), 6.54-6.51(d, 2 H), 4.93-4.76(m, 3 H), 4.16(s, 2 H), 3.41(s, 3 H), 1.43(d, 3 H) |
| 7 | —CH₂—NH— | 4-NO₂ | 8.12(d, 2 H), 7.79(s, 1 H), 7.70(s, 2 H), 7.58-7.47(m, 2 H), 6.83-6.76(mm, 2 H), 6.61(d, 2 H), 5.09-5.02(q, 1 H), 4.81(d, 1 H), 4.33(s, 2 H), 3.67(d, 1 H), 1.31(d, 3 H) |
| 8 | —CH₂—N(CH₃)— | 4-Cl | 7.95(s, 1 H), 7.81(s, 1 H), 7.43(s, 1 H), 7.38(s, 1 H), 7.15-7.12(d, 2 H), 6.98-6.95(m, 1 H), 6.85-6.79(m, 2 H), 6.58(d, 2 H), 4.91(d, 1 H), 4.83-4.76(m, 2 H), 4.16(s, 1 H), 3.41(s, 3 H), 1.43(d, 3 H) |
| 9 | —CH₂—N(CH₃)— | 4-Br | 7.97(s, 1 H), 7.95(s, 1 H), 7.43(s, 1 H), 7.38(s, 1 H), 7.28(s, 1 H), 7.25(s, 1 H), 6.98-6.96(m, 1 H), 6.83-6.76(m, 2 H), 6.52(d, 2 H), 4.93-4.76(m, 3 H), 4.16(s, 2 H), 3.41(s, 3 H), 1.43(d, 3 H) |
| 10 | —N=CH— | 4-F | 8.59(s, 1 H), 7.92(s, 1 H), 7.89-7.83(m, 3 H), 7.77(s, 1 H), 7.69(s, 1 H), 7.52(m, 1 H), 7.19-7.13(m, 2 H), 6.81-6.78(m, 2 H), 5.07-5.00(q, 1 H), 4.91(d, 1 H), 3.9(d, 1 H), 1.37(d, 3 H) |
| 11 | —NH—C(O)— | 4-F | 8.64(s, 1 H), 8.32(s, 1 H), 7.92-7.87(m, 2 H), 7.82(s, 1 H), 7.64(d, 2 H), 7.47(d, 1 H), 7.12(t, 2 H), 6.80-6.74(m, 2 H), 5.02-4.95(q, 1 H), 4.85(d, 1 H), 3.62(d, 1 H), 1.30(d, 3 H). |
| 12 | —NH—C(O)— | 4-Cl | 8.75(s, 1 H), 8.33(s, 1 H), 7.82(d, 2 H), 7.65(s, 1 H), 7.63(s, 1 H), 7.46(m, 1 H), 7.41(d, 2 H), 6.78(m, 2 H), 5.71(s, 1 H), 4.98(q, 1 H), 4.84(d, 1 H), 3.62(d, 1 H), 1.30(d, 3 H). |
| 13 | —N(CH₃)—C(O)— | 4-Cl | 7.95(s, 1 H), 7.83(s, 1 H), 7.19(m, 5 H), 6.80(m, 4 H), 4.64(m, 2 H), 3.37(s, 3 H), 3.24(d, 1 H), 1.37(d, 3 H). |
| 14 | —C(O)—N(CH₃)—C(O)— | 4-Cl | 7.74(s, 1 H), 7.71(s, 1 H), 7.53(s, 1 H), 7.43-7.39(m, 3 H), 7.21-7.18(m, 3 H), 6.98(s, 1 H), 6.79-6.73(m, 2 H), 4.91-4.89(q, 1 H), 4.76(d, 1 H), 3.41-3.40(m, 4 H), 1.27(d, 3 H). |

TABLE 1-continued

| Examples | X | $R_4$ | $^1$H-NMR (300 MHz, CDCl$_3$) δ |
|---|---|---|---|
| 15 | (ketone: -C(O)- branched) | 4-Cl | 8.15(s, 1 H), 8.11(s, 1 H), 7.94(d, 2 H), 7.64(d, 2 H), 7.5(s, 1 H), 7.4(s, 1 H), 7.15(m, 1 H), 6.67-6.61(m, 2 H), 4.52(q, 1 H), 4.31(d, 1 H), 4.05(d, 1 H), 1.61(d, 3 H) |
| 16 | (-NH-CH$_2$-C(O)-) | 4-Cl | 7.96(s, 1 H), 7.93(s, 1 H), 7.84(s, 1 H), 7.65(s, 1 H), 7.51-7.43(m, 3 H), 7.31-7.29(m, 2 H), 6.82-6.75(m, 2 H), 4.94-4.87(q, 1 H), 4.82(d, 1 H), 4.48(s, 2 H), 3.61(s, 1 H), 1.32(d, 3 H). |
| 17 | (urea with CH$_2$CH(OEt)$_2$ on N) | 4-F | 8.14(s, 1 H), 8.12(s, 1 H), 7.58(m, 2 H), 7.55(s, 1 H), 7.45(s, 1 H), 7.41(m, 2 H), 7.15(m, 1 H), 6.65(m, 2 H), 5.74(s, 1 H), 4.91(q, 1 H), 4.81(d, 1 H), 4.78(t, 1 H), 4.30(m, 2 H), 3.46(m, 3 H), 3.31(d, 2 H), 1.29(m, 9 H) |
| 18 | (urea with CH$_2$CH(OEt)$_2$ on N) | 4-Cl | 8.15(s, 1 H), 8.12(s, 1 H), 7.58(m, 2 H), 7.55(s, 1 H), 7.45(s, 1 H), 7.41(m, 2 H), 7.15(m, 1 H), 6.65(m, 2 H), 5.74(s, 1 H), 4.91(q, 1 H), 4.79(d, 1 H), 4.78(t, 1 H), 4.30(m, 2 H), 3.46(m, 3 H), 3.31(d, 2 H), 1.31(m, 9 H) |
| 19 | (urea with CH$_2$CH(OEt)$_2$ on N) | 4-CF$_3$ | 8.17(s, 1 H), 8.15(s, 1 H), 7.58(m, 2 H), 7.50(s, 1 H), 7.45(s, 1 H), 7.41(m, 2 H), 7.15(m, 1 H), 6.65(m, 2 H), 5.74(s, 1 H), 4.91(q, 1 H), 4.82(d, 1 H), 4.78(t, 1 H), 4.30(m, 2 H), 3.46(m, 3 H), 3.35(d, 2 H), 1.27(m, 9 H) |
| 20 | (urea with CH$_2$CH(OEt)$_2$ on N) | 4-tert-Bu | 8.21(s, 1 H), 8.15(s, 1 H), 7.58(m, 2 H), 7.50(s, 1 H), 7.48(s, 1 H), 7.41(m, 2 H), 7.15(m, 1 H), 6.65(m, 2 H), 5.74(s, 1 H), 4.91(q, 1 H), 4.82(d, 1 H), 4.78(t, 1 H), 4.30(m, 2 H), 3.46(m, 3 H), 3.35(d, 2 H), 1.33(s, 9 H), 1.19(m, 9 H) |
| 21 | (urea with CH$_2$CH(OEt)$_2$ on N) | 2,4-Cl | 8.15(s, 1 H), 8.12(s, 1 H), 7.86(m, 2 H), 7.55(s, 1 H), 7.41(m, 2 H), 7.15(m, 1 H), 6.65(m, 2 H), 5.74(s, 1 H), 4.91(q, 1 H), 4.79(d, 1 H), 4.78(t, 1 H), 4.30(m, 2 H), 3.46(m, 3 H), 3.31(d, 2 H), 1.29(m, 9 H) |
| 22 | (2-imidazolone) | 4-F | 8.28(s, 1 H), 7.80(s, 1 H), 7.77(s, 1 H), 7.67(s, 1 H), 7.55(m, 2 H), 7.46(m, 1 H), 7.14(m, 2 H), 6.98(m, 2 H), 6.84(m, 2 H), 5.62(s, 1 H), 5.05(q, 1 H), 4.89(d, 1 H), 3.65(d, 1 H), 1.34(d, 3 H). |

TABLE 1-continued

| Examples | X | R₄ | ¹H-NMR (300 MHz, CDCl₃) δ |
|---|---|---|---|
| 23 | imidazolidinone (with C=O) | 4-Cl | 8.28(s, 1 H), 7.80(s, 1 H), 7.76(s, 1 H), 7.68(s, 1 H), 7.58(d, 2 H), 7.51(m, 1 H), 7.41(d, 2 H), 6.79(m, 2 H), 6.72(m, 2 H), 5.59(s, 1 H), 5.05(q, 1 H), 4.89(d, 1 H), 3.65(d, 1 H), 1.35(d, 3 H). |
| 24 | imidazolidinone (with C=O) | 4-CF₃ | 8.25(s, 1 H), 7.80(s, 1 H), 7.76(s, 1 H), 7.68(s, 1 H), 7.58(d, 2 H), 7.51(m, 1 H), 7.41(d, 2 H), 6.79(m, 2 H), 6.72(m, 2 H), 5.59(s, 1 H), 5.21(q, 1 H), 4.89(d, 1 H), 3.55(d, 1 H), 1.33(d, 3 H). |
| 25 | imidazolidinone (with C=O) | 4-tert-Bu | 8.33(s, 1 H), 8.13(s, 1 H), 7.85(s, 1 H), 7.68(s, 1 H), 7.55(d, 2 H), 7.51(m, 1 H), 7.41(d, 2 H), 6.82(m, 2 H), 6.72(m, 2 H), 5.59(s, 1 H), 5.08(q, 1 H), 4.89(d, 1 H), 3.45(d, 1 H), 1.29(d, 3 H). |
| 26 | imidazolidinone (with C=O) | 2,4-Cl | 8.21(s, 1 H), 7.80(s, 1 H), 7.65(s, 1 H), 7.58(d, 2 H), 7.51(m, 1 H), 7.41(d, 2 H), 6.79(m, 2 H), 6.72(m, 2 H), 5.59(s, 1 H), 5.05(q, 1 H), 4.91(d, 1 H), 3.83(d, 1 H), 1.33(d, 3 H). |
| 27 | CH₂-piperazine | 4-F | 7.87(s, 1 H), 7.66(s, 1 H), 7.64(s, 1 H), 7.57(s, 1 H), 7.50-7.48(m, 1 H), 6.99-6.76(m, 6 H), 5.02-5.00(q, 1 H), 4.83(d, 1 H), 3.61(d, 1 H), 3.53(s, 2 H), 3.14-3.12(m, 4 H), 2.65-2.63(m, 4 H), 1.33(d, 3 H). |
| 28 | CH₂-piperazine | 4-NO₂ | 8.12(s, 1 H), 8.10(s, 1 H), 7.86(s, 1 H), 7.66(d, 2 H), 7.56(s, 1 H), 7.50-7.48(q, 1 H), 6.83-6.76(m, 4 H), 5.03-5.00(q, 1 H), 4.83(d, 1 H), 3.60(d, 1 H), 3.54(s, 2 H), 3.46-3.43(m, 4 H), 2.64-2.61(m, 4 H), 1.33(d, 3 H). |
| 29 | CH₂-piperazinone | 4-Cl | 7.85(s, 1 H), 7.68(s, 1 H), 7.65(s, 1 H), 7.60(s, 1 H), 7.49-7.47(m, 2 H), 7.37-7.35(m, 1 H), 7.27(s, 1 H), 6.80-6.75(m, 2 H), 5.02-4.99(q, 1 H), 4.82(d, 1 H), 4.44(s, 2 H), 3.68-3.62(m, 2 H), 3.59-3.52(m, 3 H), 3.40(s, 1 H), 2.87-2.83(m, 1 H), 1.30(d, 3 H). |
| 30 | C(=O)-piperazine | 4-F | 8.02(s, 1 H), 7.79(s, 1 H), 7.74(s, 1 H), 7.67(s, 1 H), 7.51(m, 1 H), 7.22(d, 2 H), 6.83(d, 2 H), 6.81(m, 2 H), 5.58(s, 1 H), 5.08(q, 1 H), 4.87(d, 1 H), 3.88(t, 4 H), 3.53(d, 1 H), 3.11(t, 4 H), 1.31(d, 3 H) |
| 31 | C(=O)-piperazine | 4-Cl | 8.07(s, 1 H), 7.81(s, 1 H), 7.74(s, 1 H), 7.67(s, 1 H), 7.48(m, 1 H), 7.22(d, 2 H), 6.83(d, 2 H), 6.77(m, 2 H), 5.58(s, 1 H), 5.08(q, 1 H), 4.87(d, 1 H), 3.88(t, 4 H), 3.67(d, 1 H), 3.19(t, 4 H), 1.33(d, 3 H). |
| 32 | C(=O)-piperazine | 4-NO₂ | 8.14(s, 1 H), 8.14(s, 1 H), 8.12(s, 1 H), 7.80(s, 1 H), 7.77(s, 1 H), 7.69(s, 1 H), 7.56(m, 1 H), 6.78(m, 4 H), 5.57(s, 1 H), 5.10(q, 1 H), 4.88(d, 1 H), 3.94(t, 4 H), 3.68(d, 1 H), 3.53(t, 4 H), 1.34(d, 3 H). |

EXAMPLES 33 to 38

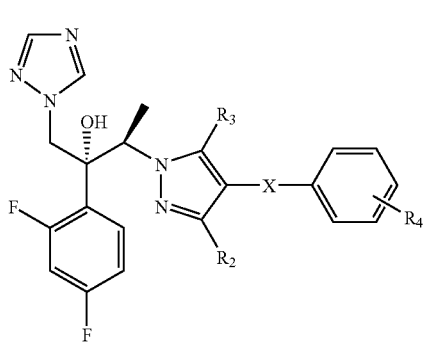

(Ib)

EXAMPLES 38 to 50

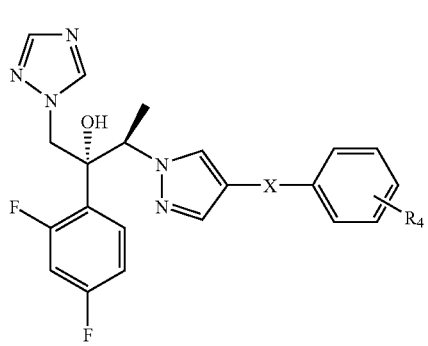

(Ic)

Procedures similar to that of Example 1 were performed to synthesize various compounds represented by formula (Ib), X, $R_2$, $R_3$ and $R_4$ being listed in Table 2:

Procedures similar to that of Example 2 were performed to synthesize various compounds represented by formula (Ic), X, and $R_4$ being listed in Table 3:

TABLE 2

| Examples | X | $R_2$ | $R_3$ | $R_4$ | $^1$H-NMR (300 MHz, CDCl$_3$) δ |
|---|---|---|---|---|---|
| 33 | ~~~C(O)NH~~~ | CH$_3$ | H | 4-F | 8.15(s, 1 H), 8.11(s, 1 H), 7.62(s, 2 H), 7.3(s, 1 H), 7.15(s, 3 H), 6.67-6.61(m, 2 H), 4.33-4.30(m, 3 H), 2.79(s, 3 H), 1.61(s, 3 H) |
| 34 | ~~~C(O)NH~~~ | CH$_3$ | H | 4-Cl | 8.17(s, 1 H), 7.86(m, 2 H), 7.71(s, 1 H), 7.60(m, 3 H), 7.30(m, 2 H), 5.66(s, 1 H), 5.01(q, 1 H), 4.87(d, 1 H, J = 14.3 Hz), 3.71(d, 1 H, J = 14.2 Hz), 2.58(s, 3 H), 1.39(d, 3 H) |
| 35 | ~~~C(O)N(CH$_3$)~~~ | CH$_3$ | H | 4-Cl | 7.74(s, 1 H), 7.71(s, 1 H), 7.53(s, 1 H), 7.43-7.39(m, 3 H), 7.21-7.18(m, 3 H), 6.98(s, 1 H), 6.79-6.73(m, 2 H), 4.91-4.89(q, 1 H), 4.76(d, 1 H), 3.41-3.40(m, 4 H), 1.27(d, 3 H). |
| 36 | ~~~CH$_2$C(O)-piperazine-N~~~ | CH$_3$ | H | 4-Cl | 8.32(s, 1 H), 8.28(s, 1 H), 7.92(s, 2 H), 7.75(s, 1 H), 7.53(m, 1 H), 6.89(m, 4 H), 5.70(s, 1 H), 5.01(q, 1 H), 4.83(d, 1 H), 3.86(t, 4 H), 3.78(d, 1 H), 3.50(t, 4 H), 2.53(s, 3 H), 1.38(d, 3 H) |
| 37 | ~~~CH$_2$C(O)-piperazine-N~~~ | CH$_3$ | H | 4-NO$_2$ | 8.15(s, 1 H), 8.12(s, 1 H), 7.82(s, 2 H), 7.69(s, 1 H), 7.49(m, 1 H), 6.80(m, 4 H), 5.74(s, 1 H), 5.01(q, 1 H), 4.83(d, 1 H), 3.86(t, 4 H), 3.78(d, 1 H), 3.50(t, 4 H), 2.40(s, 3 H), 1.30(d, 3 H). |

TABLE 3

| Examples | X | R₄ | ¹H-NMR (300 MHz, CDCl₃) δ |
|---|---|---|---|
| 38 | -CH₂-CH₂-CH₂- | 4-F | 8.00 (s, 1 H), 7.71(s, 1 H), 7.48-7.46(m, 1 H), 7.41(s, 1 H), 7.34(s, 1 H), 7.13-7.08(m, 2 H), 6.97-6.91(m, 2 H), 6.81-6.76(m, 2 H), 5.01-4.94(q, 1 H), 4.83(d, 1 H), 3.50(d, 1 H), 2.90-2.77(m, 4 H), 1.28(d, 3 H). |
| 39 | -CH₂-CH₂-CH₂- | 4-Cl | 7.99(s, 1 H), 7.72(s, 1 H), 7.52-7.32(m, 3 H), 7.24-7.21(d, 2 H), 7.16-7.06(m, 2 H), 6.82-6.76(m, 2 H), 4.98(q, 1 H), 4.79(d, 1 H), 3.48(d, 1 H), 2.90-2.81(m, 4 H), 1.28(d, 3 H). |
| 40 | -CH=CH-CH₂- | 4-F | 7.92(s, 1 H), 7.80(s, 1 H), 7.77(s, 1 H), 7.69(s, 1 H), 7.56-7.39(m, 3 H), 7.07-7.01(m, 2 H), 6.87(s, 2 H), 6.84-6.77(m, 2 H), 5.08-5.01(q, 1 H), 4.88(d, 1 H), 3.67(d, 1 H), 1.34(d, 3 H). |
| 41 | -CH=CH-CH₂- | 4-Cl | 7.83(s, 1 H), 7.82(s, 1 H), 7.77(s, 1 H), 7.68(s, 1 H), 7.39-7.29(m, 4 H), 6.97-6.77(m, 4 H), 5.75(s, 1 H), 5.08-5.01(q, 1 H), 4.87(d, 1 H), 3.65(d, 1 H), 1.34(d, 3 H). |
| 42 | -CH=CH-CH₂- | 4-NO₂ | 8.22(s, 1 H), 8.19(s, 1 H), 8.12(s, 1 H), 7.89(s, 1 H), 7.82(s, 1 H), 7.75(s, 1 H), 7.57(s, 1 H), 7.54(s, 1 H), 7.50-7.45(m, 1 H), 7.12(d, 1 H), 6.96(d, 1 H), 6.85-6.78(m, 2 H), 5.10-5.03(q, 1 H), 4.91(d, 1 H), 3.72(d, 1 H), 1.35(d, 3 H). |
| 43 | -CH=CH-CH₂- | 4-CF₃ | 7.87(s, 1 H), 7.84(s, 1 H), 7.79(s, 1 H), 7.69 (s, 1 H), 7.61-7.49(m, 5 H), 7.07(d, 1 H), 6.86(d, 1 H), 6.88-6.78(m, 2 H), 5.73(s, 1 H), 5.10-4.98(q, 1 H), 4.88(d, 1 H), 3.67(d, 1 H), 1.40(d, 3 H). |
| 44 | -CH=CH-CH₂- | 3,4-Cl | 7.85(s, 1 H), 7.83(s, 1 H), 7.76(s, 1 H), 7.69(s, 1 H), 7.54-7.74(m, 2 H), 7.40(d, 1 H), 7.27-7.24(m, 1 H), 6.96(d, 1 H), 6.80-6.75(m, 3 H), 5.05(q, 1 H), 4.87(d, 1 H), 3.66(d, 1 H), 1.34(d, 3 H). |
| 45 | -C≡C- | 4-F | 7.94(s, 1 H), 7.83(s, 1 H), 7.73(s, 1 H), 7.71(s, 1 H), 7.50-7.45(m, 3 H), 7.07-7.01(m, 2 H), 6.83-6.77(m, 2 H), 5.59(bs, 1 H), 5.10-5.03(q, 1 H), 4.89(d, 1 H), 3.63(d, 1 H), 1.35(d, 3 H). |
| 46 | -C≡C- | 2,4-F | 7.97(s, 1 H), 7.84(s, 1 H), 7.75(s, 1 H), 7.71(s, 1 H), 7.49-7.45(m, 2 H), 6.90-6.77(m, 4 H), 5.58(bs, 1 H), 5.08-5.03(q, 1 H), 4.89(d, 1 H), 3.63(d, 1 H), 1.34(d, 3 H). |
| 47 | -C≡C- | 3-CH₃, 4-F | 7.92(s, 1 H), 7.88(s, 1 H), 7.73(s, 1 H), 7.72(s, 1 H), 7.53-7.48(m, 1 H), 7.35-7.29(m, 2 H), 7.00-6.94(m, 1 H), 6.83-6.77(m, 2 H), 5.06(q, 1 H), 4.89(d, 1 H), 3.64(d, 1 H), 2.27(s, 3 H), 1.34(d, 3 H). |
| 48 | -C≡C- | 4-CN | 8.15(s, 1 H), 8.11(s, 1 H), 7.60(d, 2 H), 7.50(s, 1 H), 7.48(d, 2 H), 7.40(s, 1 H), 7.15(d, 1 H), 6.67-6.61(m, 2 H), 4.32(q, 1 H), 4.30(d, 1 H), 4.05(d, 1 H), 1.61(d, 3 H). |
| 49 | cyclopropyl | 4-F | 8.15(s, 1 H), 8.11(s, 1 H), 7.31(s, 1 H), 7.19(s, 1 H), 7.15(d, 1 H), 7.04(d, 2 H), 6.85(d, 2 H), 6.67-6.61(m, 2 H), 4.32(q, 1 H), 4.30(d, 1 H), 4.05(d, 1 H), 3.81(s, 2 H), 1.61(d, 3 H). |
| 50 | cyclopropyl | 4-Cl | 8.13(s, 1 H), 8.10(s, 1 H), 7.30(s, 1 H), 7.17(s, 1 H), 7.11(m, 3 H), 7.00(d, 2 H), 6.65-6.61(m, 2 H), 4.32(q, 1 H), 4.28(d, 1 H), 4.06(d, 1 H), 3.81(s, 2 H), 1.60(d, 3 H). |

EXAMPLES 51 to 65

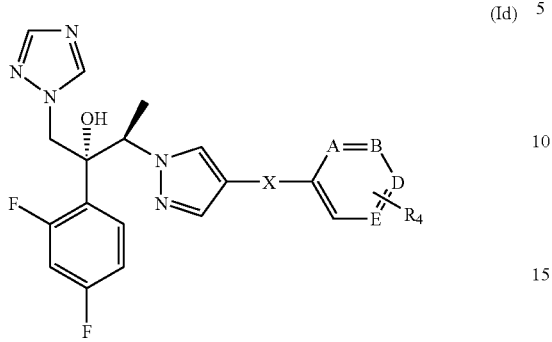

Procedures similar to that of Example 2 were performed to synthesize various compounds represented by formula (Id), X, A, B, D, E and $R_4$ being listed in Table 4:

TABLE 4

| Examples | X | A | B | D | E | $R_4$ | $^1$H-NMR (300 MHz, CDCl$_3$) δ |
|---|---|---|---|---|---|---|---|
| 51 | ⤳=⤳ | N | C | C | C | H | 8.63(d, 1 H), 8.15(s, 1 H), 8.11(s, 1 H), 7.61-7.60(m, 2 H), 7.50-7.40(m, 3 H), 7.27(t, 2 H), 7.20-7.15(m, 2 H), 6.67-6.61(m, 2 H), 4.32(q, 1 H), 4.30(d, 1 H), 4.05(d, 1 H), 1.61(d, 3 H). |
| 52 | ⤳=⤳ | C | C | C | N | H | 8.71(d, 2 H), 8.15(s, 1 H), 8.11(s, 1 H), 7.51-7.50(m, 3 H), 7.40(s, 1 H), 7.29(d, 1 H), 7.15(d, 1 H), 6.97(d, 1 H), 6.67-6.61(m, 2 H), 4.32(q, 1 H), 4.30(d, 1 H), 4.05(d, 1 H), 1.61(d, 3 H). |
| 53 | ⤳=⤳ | N | C | C | N | H | 8.58(s, 1 H), 8.51(s, 1 H), 8.38(s, 1 H), 7.92(s, 1 H), 7.84(s, 2 H), 7.69(s, 1 H), 7.65(d, 1 H), 7.54-7.46(m, 1 H), 6.95(d, 1 H), 6.83-6.77(m, 2 H), 5.71(bs, 1 H), 5.07(q, 1 H), 4.88(d, 1 H), 3.67(d, 1 H), 1.35(d, 3 H). |
| 54 | ⤳=⤳ | N | C | C | C | 3-CH$_3$ | 8.15(s, 1 H), 8.11(s, 1 H), 7.60(m, 2 H), 7.50(s, 1 H), 7.40(s, 1 H), 7.20-7.15(m, 3 H), 6.67-6.61(m, 2 H), 4.32(q, 1 H), 4.30(d, 1 H), 4.05(d, 1 H), 2.55(s, 3 H), 1.61(d, 3 H). |
| 55 | ⤳=⤳ | N | C | C | C | 4-NO$_2$ | 9.56(s, 1 H), 8.54(d, 1 H), 8.15(s, 1 H), 8.11(s, 1 H), 7.75(d, 1 H), 7.60(d, 1 H), 7.50(s, 1 H), 7.40(s, 1 H), 7.20(d, 1 H), 7.15(d, 1 H), 6.67-6.61(m, 2 H), 4.32(q, 1 H), 4.30(d, 1 H), 4.05(d, 1 H), 1.61(d, 3 H). |
| 56 | ⤳=⤳ | N | C | C | C | 4-NO$_2$ 6-CH$_3$ | 9.54(s, 1 H), 8.48(s, 1 H), 8.15(s, 1 H), 8.11(s, 1 H), 7.60(d, 1 H), 7.50(s, 1 H), 7.40(s, 1 H), 7.20(d, 1 H), 7.15(d, 1 H), 6.67-6.61(m, 2 H), 4.32(q, 1 H), 4.30(d, 1 H), 4.05(d, 1 H), 2.32(d, 3 H), 1.61(d, 3 H). |

TABLE 4-continued

| Examples | X | A | B | D | E | R₄ | ¹H-NMR (300 MHz, CDCl₃) δ |
|---|---|---|---|---|---|---|---|
| 57 | –CH=CH– | C | N | C | C | 4-NO₂ | 8.89(s, 1 H), 8.46-8.42(m, 2 H), 8.15(s, 1 H), 8.11(s, 1 H), 7.50(s, 1 H), 7.40(s, 1 H), 7.15(d, 1 H), 6.99(m, 2 H), 6.67-6.61(m, 2 H), 4.32(q, 1 H), 4.30(d, 1 H), 4.05(d, 1 H), 1.61(d, 3 H). |
| 58 | –CH=CH– | C | N | C | C | 5-CN | 9.13(s, 1 H), 9.10(s, 1 H), 8.51(s, 1 H), 8.15(s, 1 H), 8.11(s, 1 H), 7.50(s, 1 H), 7.40(s, 1 H), 7.15(d, 1 H), 6.99(m, 2 H), 6.67-6.61(m, 2 H), 4.32(q, 1 H), 4.30(d, 1 H), 4.05(d, 1 H), 1.61(d, 3 H). |
| 59 | –CH=CH– | N | C | C | C | 4-Cl | 8.83(s, 1 H), 8.15(s, 1 H), 8.11(s, 1 H), 7.85(d, 1 H), 7.68(d, 1 H), 7.60(d, 1 H), 7.50(s, 1 H), 7.40(s, 1 H), 7.20(d, 1 H), 6.65-6.61(m, 2 H), 4.31(q, 1 H), 4.30(d, 1 H), 4.04(d, 1 H), 1.61(d, 3 H). |
| 60 | –C≡C– | N | C | C | C | H | 8.56(d, 1 H), 8.15(s, 1 H), 8.11(s, 1 H), 7.72(t, 1 H), 7.54-7.36(m, 4 H), 7.15(d, 1 H), 6.67-6.61(m, 2 H), 4.32(q, 1 H), 4.30(d, 1 H), 4.05(d, 1 H), 1.61(d, 3 H). |
| 61 | –C≡C– | C | N | C | C | H | 8.75(s, 1 H), 8.57(d, 1 H), 8.15(s, 1 H), 8.11(s, 1 H), 7.91(d, 1 H), 7.50(s, 1 H), 7.40-7.35(m, 2 H), 7.15(d, 1 H), 6.67-6.61(m, 2 H), 4.32(q, 1 H), 4.30(d, 1 H), 4.05(d, 1 H), 2.32(d, 3 H), 1.61(d, 3 H). |
| 62 | –C≡C– | N | C | C | C | 4-NO₂ | 9.49(s, 1 H), 8.65(d, 1 H), 8.15(s, 1 H), 8.11(s, 1 H), 7.80(d, 1 H), 7.50(s, 1 H), 7.40(s, 1 H), 7.15(d, 1 H), 6.67-6.61(m, 2 H), 4.32(q, 1 H), 4.30(d, 1 H), 4.05(d, 1 H), 1.61(d, 3 H). |
| 63 | –C≡C– | C | N | C | C | 4-NO₂ | 9.01(s, 1 H), 8.58(d, 1 H), 8.44(d, 1 H), 8.15(s, 1 H), 8.11(s, 1 H), 7.50(s, 1 H), 7.40(s, 1 H), 7.15(d, 1 H), 6.67-6.61(m, 2 H), 4.32(q, 1 H), 4.30(d, 1 H), 4.05(d, 1 H), 1.61(d, 3 H). |
| 64 | –C≡C– | N | C | C | C | 4-NO₂ 6-CH₃ | 9.47(s, 1 H), 8.59(d, 1 H), 8.15(s, 1 H), 8.11(s, 1 H), 7.80(d, 1 H), 7.50(s, 1 H), 7.40(s, 1 H), 7.15(d, 1 H), 6.67-6.61(m, 2 H), 4.32(q, 1 H), 4.30(d, 1 H), 4.05(d, 1 H), 2.32(d, 3 H), 1.61(d, 3 H). |
| 65 | –C≡C– | N | C | C | C | 4-Cl | 8.76(s, 1 H), 8.15(s, 1 H), 8.11(s, 1 H), 7.96(d, 1 H), 7.73(d, 1 H), 7.52(s, 1 H), 7.41(s, 1 H), 7.14(d, 1 H), 6.68-6.60(m, 2 H), 4.31(q, 1 H), 4.30(d, 1 H), 4.05(d, 1 H), 1.61(d, 3 H). |

EXAMPLES 66 to 68

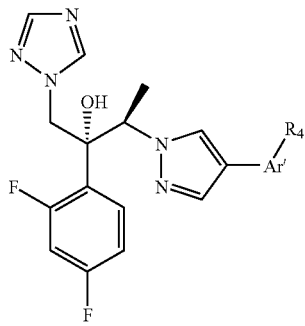

(Ie)

Procedures similar to that of Example 2 were performed to synthesize various compounds represented by formula (Ie), Ar' (a benzene ring fused with a 5- or 6-membered heterocyclic ring containing one or more heteroatoms selected from N, O and S) and $R_4$ being listed in Table 5:

mixed with lactose (65 mg) and corn starch (30 mg) for 30 min using a mechanical shaker and a mixer. The mixture was pressed into tablets.

TEST EXAMPLE 1

In Vitro Assay for Antifungal Activity

Each fungal strain to be tested was inoculated onto Sabouraud dextrose agar, YM agar, and potato dextrose agar and cultured at 35° C. for two to three days. Single colonies of such of the yeast fungi were collected from the culture and suspended in 5 ml of 0.85% sterile saline, in an appropriate amount so that the absorbance at 530 nm became 0.108. The suspensions was diluted serially by 1:50 (RPMI 1640 media:sterile saline) and then further diluted by 1:20 (RPMI 1640 media:sterile saline) to prepare liquid inocula having a cell count ranging from $1.0 \times 10^3$ to $5.0 \times 10^3$ CFU/ml.

Antifungal samples were prepared by serially diluting each of the compounds of the present invention in RPMI 1640 media to concentrations range from 0.0156 to 32 µg/ml. As an excipient, DMSO was added to the antifungal sample to a final concentration of 1% (VAT). 0.1 ml of each of the serially diluted test solution was added to each well of 96 well plate, followed by adding 0.1 ml of each of the fungal inocula thereto.

TABLE 5

| Examples | $Ar^1$ | $R_4$ | $^1$H-NMR (300 MHz, CDCl$_3$) δ |
|---|---|---|---|
| 66 | (4-quinolinyl) | H | 8.91(d, 1 H), 8.21-8.16(m, 2 H), 8.10(s, 1 H), 7.93(s, 1 H), 7.87(s, 1 H), 7.76(t, 1 H), 7.71(s, 1 H), 7.61-7.58(m, 2 H), 7.40(d, 1 H), 6.85-6.79(m, 2 H), 5.79(s, 1 H), 5.19(q, 1 H), 4.96(d, 1 H), 3.82(d, 1 H), 1.45(s, 3 H). |
| 67 | (2-quinoxalinyl) | H | 9.11(s, 1 H), 8.52(s, 1 H), 8.30(s, 1 H), 8.10-8.01(m, 2 H), 7.83-7.68(m, 3 H), 7.53(t, 1 H), 7.71(s, 1 H), 6.82-6.78(m, 2 H), 5.69(s, 1 H), 5.18(q, 1 H), 4.97(d, 1 H), 3.75(d, 1 H), 1.43(s, 3 H). |
| 68 | (2-benzofuranyl) | H | 8.14(s, 1 H), 7.96(s, 1 H), 7.83(s, 1 H), 7.69(s, 1 H), 7.56-7.48(m, 3 H), 7.72-7.23(m, 2 H), 6.81-6.78(m, 2 H), 5.68(s, 1 H), 5.11(q, 1 H), 4.93(d, 1 H), 3.70(d, 1 H), 1.39(s, 3 H). |

FORMULATION EXAMPLE 1

Tablet

Each of the compounds (50 mg) prepared in the Examples and magnesium stearate (20 mg) were granulated with soluble starch (35 mg). Then the granules were dried and At a given concentration of the test compound, the fungus growth was observed, after 24 hours, with the naked eye for all yeast species except for *Cryptococcus neoformans*, and the filamentous fungus growth was observed, after 48 hours. Also, using the growth indicator alamarBlue, $MIC_{80}$, the concentration of the test compound at which 80% inhibition of the fungus growth occurs was determined based on the value observed for the negative control.

All tests were conducted in duplicate for each test group, and the results are given in Table 6:

TABLE 6

| | In vitro Assay for Antifungal Activity ($MIC_{80}$ µg/ml) | | | | | |
|---|---|---|---|---|---|---|
| Examples | Candida albicans | Candida glabrata | Candida krusei | Candida tropicallis | Candida parapsilosis | Cryptococcus neoformans |
| 1 | ≦0.015 | 8 | 2 | 1 | 0.125 | 0.25 |
| 23 | ≦0.015 | 4 | 0.5 | 0.125 | ≦0.015 | 0.125 |
| 38 | ≦0.015 | 2 | 0.25 | ≦0.015 | ≦0.015 | 0.125 |
| 39 | ≦0.015 | 1 | 0.5 | 0.062 | ≦0.015 | ≦0.015 |
| 40 | ≦0.015 | 2 | 0.25 | ≦0.015 | ≦0.015 | 0.031 |
| 41 | ≦0.015 | 1 | 0.5 | 0.125 | ≦0.015 | ≦0.015 |
| 45 | ≦0.015 | 2 | 0.5 | ≦0.015 | ≦0.015 | 0.062 |
| 53 | 0.125 | — | 4 | — | 0.125 | 1 |
| Fluconazole | 4 | >32 | 4 | >32 | >32 | 32 |

TEST EXAMPLES 2

In Vivo Assay for Antifungal Activity 0.1 mL of a suspension containing 5×10⁷ CFU/ml of *Candida albicans* was administered to each of 10 male mice by intravenous injection. 10 mg/kg of each of the test compounds to orally administer to the inoculated mouse 2 hours after the fungal infection. The test compound was administered once a day for seven days. The number of mice which survived the fungal infection for 28 days after the fungal infection was determined as % survival for each test group, and the results are given in Table 7:

TABLE 7

| | Control (10% ethanol-polyethylene glycol) | Ex. 41 | Ex. 45 | Fluconazole |
|---|---|---|---|---|
| % Survival | 0 | 100 | 100 | 50 |

TEST EXAMPLE 3

Assay for Subacute Toxicity in Mice

Subacute cytotoxicity tests were conducted by administering Example compounds 41 and 45, each suspended in aqueous 0.5% methylcellulose to mice once a day for 2 weeks. As a result, none of the mice were observed to suffer from toxic syndromes, showing no changes in the living states, organs, liver enzyme and liver weight.

As described hereinbefore, the inventive compound of formula (I), or an isomer or pharmaceutically acceptable salt thereof showed an excellent antifungal activity as well as being safe in vivo. Therefore, the compounds of formula (I) of the present invention can be useful for treating fungal infections.

While the invention has been described with respect to the above specific embodiments, it should be recognized that various modifications and changes may be made to the invention by those skilled in the art which also fall within the scope of the invention as defined by the appended claims.

What is claimed is:

1. A compound of formula (I), or an isomer or pharmaceutically acceptable salt thereof:

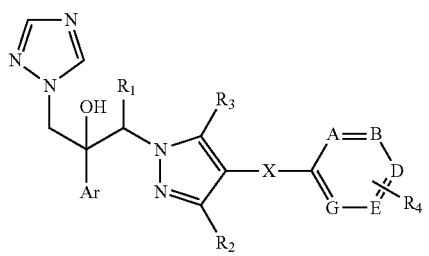

wherein,

Ar is phenyl substituted with at least one halogen or $C_1$-$C_4$ haloalkyl;

$R_1$ is hydrogen, fluorine or $C_1$-$C_4$ alkyl;

$R_2$, $R_3$ and $R_4$ are each independently hydrogen, halogen, $C_1$-$C_4$ alkyl, $C_1$-$C_4$ haloalkyl, $C_3$-$C_6$ cycloalkyl, $C_1$-$C_4$ alkoxy, nitro, cyano, amino, hydroxy, —$NR_5R_6$, —$CONR_5R_6$, —$CH_2$—CO—$R_5$, —$CH_2$—OCO—$R_5$, —CO—$R_5$, —$COOR_5$, —C(=$NR_5$)$NHR_7$, —C(=$NR_7$)$OR_7$, —$SO_2R_7$, —$NR_5SO_2R_7$ or aryl $C_1$-$C_4$ alky, the aryl moiety being phenyl or naphtyl unsubstituted or substituted with at least one halogen, $C_1$-$C_4$ alkyl, $C_1$-$C_4$ haloalkyl, $C_1$-$C_4$ haloalkoxy, nitro, cyano, hydroxy or hydroxymethyl, wherein $R_4$ may represent two or more substituents independently selected from the above-mentioned substituents;

X is $C_1$-$C_4$ alkyl, $C_2$-$C_4$ alkenyl or $C_2$-$C_4$ alkynyl unsubstituted or substituted with at least one halogen; O; $NR_2$; $CONR_2$;

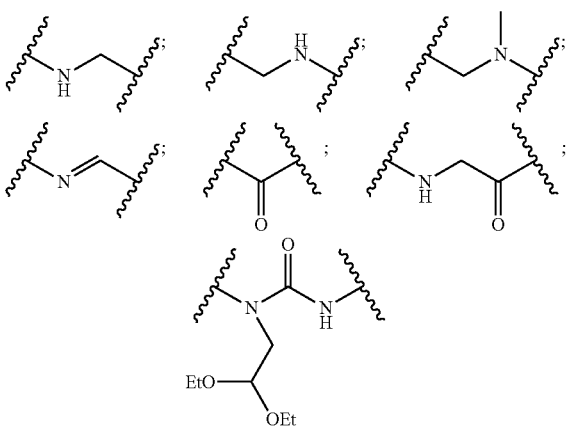

or Q-P unsaturated or substituted with O or $C_1$-$C_4$alky; Q being a linker, CO or $C_1$-$C_4$ alkyl, and P being a 5- to 7-membered heterocyclic ring containing at least one nitrogen or oxygen atom; and A, B, D, E and G are each independently nitrogen or carbon fused together to form a phenyl, pyridine, pyrimidine or triazine group, which is optionally fused with X to form a ring, in which $R_5$ is hydrogen, $C_1$-$C_4$ alkyl, $C_3$-$C_6$ cycloalkyl, —COCF$_3$, or the aryl $C_1$-$C_4$ alkyl defined for $R_2$;

$R_6$ is hydrogen, —CONH$_2$, —COCH$_3$, —CN, or —($C_1$-$C_4$ alkyl)-NH$_2$;

$R_7$ is $C_1$-$C_4$ alkyl, $C_3$-$C_6$ cylcoalkyl, or the aryl $C_1$-$C_4$ alkyl defined for $R_2$; and Z is 0, 1, or 2.

2. The compound of claim 1, wherein:
$C_1$-$C_4$ alkyl is methyl, ethyl, propyl, isopropyl, butyl, isobutyl, sec-butyl or tert-butyl;
$C_1$-$C_4$ haloalkyl is trifluoromethyl, trichloromethyl, fluoromethyl, chloromethyl, bromomethyl, iodomethyl, difluoromethyl, dichloromethyl, 2-chloroethyl, 2,2-dichloroethyl, 2,2,2-trichloroethyl, pentachloroethyl, 2-fluoroethyl, 2,2-difluoroethyl, 2,2,2-trifluoroethyl, pentafluoroethyl, 3-chloropropyl, 3,3-dichloropropyl, 3,3,3-trichloropropyl, 2,2,3,3,3-pentachloropropyl, 3-fluoropropyl, 3,3-difluoropropyl, 3,3,3-trifluoropropyl, 2,2,3,3-tetrafluoropropyl, 2,2,3,3,3-pentafluoropropyl, heptafluoropropyl, 4-chlorobutyl, 4-fluorobutyl, 4-iodobutyl or 4-bromobutyl;
$C_3$-$C_6$ cycloalkyl is cyclopropyl, cyclobutyl, cyclopentyl or cyclohexyl;
$C_1$-$C_4$ alkoxy is methoxy, ethoxy, propoxy, isopropoxy, butoxy, isobutoxy, sec-butoxy or tert-butoxy;
$C_1$-$C_4$ haloalkoxy is trifluoromethoxy, fluoromethoxy, 2-chloroethoxy, 2-fluoroethoxy, 2,2-difluoroethoxy, 2-iodoethoxy, 2,2-difluoroethoxy, 2,2,2-trifluoroethoxy, pentafluoroethoxy, 3-fluoropropoxy, 3-chloropropoxy, 2,2,3,3-tetrafluoropropoxy, 2,2,3,3,3-pentafluoropropoxy, heptafluoropropoxy, 4-fluorobutoxy or 4-chlorobutoxy;
halogen is fluorine, chlorine, bromine or iodine; and
aryl $C_1$-$C_4$ alkyl is a $C_1$-$C_4$ alkyl group having a phenyl or naphthyl substituent.

3. The compound of claim 1, wherein $R_2$, $R_3$ and $R_4$ are each independently hydrogen, halogen, $C_1$-$C_4$ alkyl, $C_1$-$C_4$ haloalkyl, $C_3$-$C_6$ cycloalkyl, $C_1$-$C_4$ alkoxy, nitro, cyano, amino or hydroxy, wherein $R_4$ may represent two or more substituents independently selected from the above-mentioned substituents.

4. The compound of claim 1, which is selected from the group consisting of:
1) 1-(4-Chlorophenyl)-3-(1-((2R,3R)-3-(2,4-difluorophenyl)-3-hydroxy-4-(1H-1,2,4-triazol-1-yl)butan-2-yl)-1H-pyrazol-4-yl)imidazolidin-2-one;
2) 4-((E)-2-(1-((2R,3R)-3-(2,4-Difluorophenyl)-3-hydroxy-4-(1H-1,2,4-triazol-1-yl)butan-2-yl)-1H-pyrazol-4-yl)vinyl)benzonitrile;
3) (2R,3R)-2-(2,4-Difluorophenyl)-3-((4-(4-fluorobenzyl)amino)-1H-pyrazol-1-yl)-1-(1H-1,2,4-triazol-1-yl)butan-2-ol;
4) (2R,3R)-3-(4-((4-Chlorobenzyl)amino)-1H-pyrazol-1-yl)-2-(2,4-difluorophenyl)-1-(1H-1,2,4-triazol-1-yl)butan-2-ol;
5) (2R,3R)-3-(4-(((4-Chlorophenyl)amino)methyl)-1H-pyrazol-1-yl)-2-(2,4-difluorophenyl)-1-(1H-1,2,4-triazol-1-yl)butan-2-ol;
6) (2R,3R)-3-(4-(((4-Bromophenylamino)methyl)-1H-pyrazol-1-yl)-2-(2,4-difluorophenyl)-1-(1H-1,2,4-triazol-1-yl)butan-2-ol;
7) (2R,3R)-2-(2,4-Difluorophenyl)-3-(4-(((4-nitrophenyl)amino)methyl)-1H-pyrazol-1-yl)-1-(1H-1,2,4-triazol-1-yl)butan-2-ol;
8) (2R,3R)-3-(4-(((4-Chlorophenyl)(methyl)amino)methyl)-1H-pyrazol-1-yl)-2-(2,4-difluorophenyl)-1-(1H-1,2,4-triazol-1-yl)butan-2-ol;
9) (2R,3R)-3-(4-(((4-Bromophenyl)(methyl)amino)methyl)-1H-pyrazol-1-yl)-2-(2,4-difluorophenyl)-1-(1H-1,2,4-triazol-1-yl)butan-2-ol;
10) (2R,3R)-2-(2,4-Difluorophenyl)-3-(4-((E)-(4-fluorobenzylidene)amino)-1H-pyrazol-1-yl)-1-(1H-1,2,4-triazol-1-yl)butan-2-ol;
11) N-(1-((2R,3R)-3-(2,4-Difluorophenyl)-3-hydroxy-4-(1H-1,2,4-triazol-1-yl)butan-2-yl)-1H-pyrazol-4-yl)-4-fluorobenzamide;
12) 4-Chloro-N-(1-((2R,3R)-3-(2,4-difluorophenyl)-3-hydroxy-4-(1H-1,2,4-triazol-1-yl)butan-2-yl)-1H-pyrazol-4-yl)-benzamide;
13) 4-Chloro-N-(1-((2R,3R)-3-(2,4-difluorophenyl)-3-hydroxy-4-(1H-1,2,4-triazol-1-yl)butan-2-yl)-1H-pyrazol-4-yl)-N-methylbenzamide;
14) N-(4-Chlorophenyl)-1-((2R,3R)-3-(2,4-difluorophenyl)-3-hydroxy-4-(1H-1,2,4-triazol-1-yl)butan-2-yl)-N-methyl-1H-pyrazole-4-carboxamide;
15) (4-Chlorophenyl)(1-((2R,3R)-3-(2,4-difluorophenyl)-3-hydroxy-4-(1H-1,2,4-triazol-1-yl)butan-2-yl)-1H-pyrazol-4-yl)methanone;
16) 1-(4-Chlorophenyl)-2-(1-((2R,3R)-3-(2,4-difluorophenyl)-3-hydroxy-4-(1H-1,2,4-triazol-1-yl)butan-2-yl)-1H-pyrazol-4-ylamino)ethanone;
17) 1-(2,2-Diethoxyethyl)-1-(1-((2R,3R)-3-(2,4-difluorophenyl)-3-hydroxy-4-(1H-1,2,4-triazol-1-yl)butan-2-yl)-1H-pyrazol-4-yl)-3-(4-fluorophenyl)urea;
18) 3-(4-Chlorophenyl)-1-(2,2-diethoxyethyl)-1-(1-((2R,3R)-3-(2,4-difluorophenyl)-3-hydroxy-4-(1H-1,2,4-triazol-1-yl)butan-2-yl)-1H-pyrazol-4-yl)urea;
19) 1-(2,2-Diethoxyethyl)-1-(1-((2R,3R)-3-(2,4-difluorophenyl)-3-hydroxy-4-(1H-1,2,4-triazol-1-yl)butan-2-yl)-1H-pyrazol-4-yl)-3-(4-(trifluoromethyl)phenyl)urea;
20) 3-(4-(Tert-butyl)phenyl)-1-(2,2-diethoxyethyl)-1-(1-((2R,3R)-3-(2,4-difluorophenyl)-3-hydroxy-4-(1H-1,2,4-triazol-1-yl)butan-2-yl)-1H-pyrazol-4-yl)urea;
21) 3-(2,4-Dichlorophenyl)-1-(2,2-diethoxyethyl)-1-(1-((2R,3R)-3-(2,4-difluorophenyl)-3-hydroxy-4-(1H-1,2,4-triazol-1-yl)butan-2-yl)-1H-pyrazol-4-yl)urea;
22) 1-(1-((2R,3R)-3-(2,4-Difluorophenyl)-3-hydroxy-4-(1H-1,2,4-triazol-1-yl)butan-2-yl)-1H-pyrazol-4-yl)-3-(4-fluorophenyl)-1H-imidazol-2(3H)-one;
23) 1-(4-Chlorophenyl)-3-(1-((2R,3R)-3-(2,4-difluorophenyl)-3-hydroxy-4-(1H-1,2,4-triazol-1-yl)butan-2-yl)-1H-pyrazol-4-yl)-1H-imidazole-2(3H)-one;
24) 1-(1-((2R,3R)-3-(2,4-Difluorophenyl)-3-hydroxy-4-(1H-1,2,4-triazol-1-yl)butan-2-yl)-1H-pyrazol-4-yl)-1H-3-(4-(trifluoromethyl)phenyl)-imidazole-2(3H)-one;
25) 1-(4-Tert-butylphenyl)-3-(1-((2R,3R)-3-(2,4-difluorophenyl)-3-hydroxy-4(1H-1,2,4-triazol-1-yl)butan-2-yl)-1H-pyrazol-4-yl)-1H-imidazole-2(3H)-one;
26) 1-(2,4-Dichlorophenyl)-3-(1-((2R,3R)-3-(2,4-difluorophenyl)-3-hydroxy-4-(1H-1,2,4-triazol-1-yl)butan-2-yl)-1H-pyrazol-4-yl)-1H-imidazole-2(3H)-one;

27) (2R,3R)-2-(2,4-Difluorophenyl)-3-(4-((4-(4-fluorophenyl)piperazin-1-yl)methyl)-1H-pyrazol-1-yl)-1-(1H-1,2,4-triazol-1-yl)butan-2-ol;
28) (2R,3R)-2-(2,4-Difluorophenyl)-3-(4-((4-(4-nitrophenyl)piperazin-1-yl)methyl)-1H-pyrazol-1-yl)-1-(1H-1,2,4-triazol-1-yl)butan-2-ol;
29) (2R,3R)-3-(4-((4-(4-Chlorophenyl)piperazin-1-yl)methyl)-1H-pyrazol-1-yl)-2-(2,4-difluorophenyl)-1-(1H-1,2,4-triazol-1-yl)butan-2-ol;
30) (1-((2R,3R)-3-(2,4-Difluorophenyl)-3-hydroxy-4-(1H-1,2,4-triazol-1-yl)butan-2-yl)-1H-pyrazol-4-yl)(4-(4-fluorophenyl)piperazin-1-yl)-methanone;
31) (4-(4-Chlorophenyl)piperazin-1-yl)(1-((2R,3R)-3-(2,4-difluorophenyl)-3-hydroxy-4-(1H-1,2,4-triazol-1-yl)butan-2-yl)-1H-pyrazol-4-yl)methanone;
32) (1-((2R,3R)-3-(2,4-Difluorophenyl)-3-hydroxy-4-(1H-1,2,4-triazol-1-yl)butan-2-yl)-1H-pyrazol-4-yl)(4-(4-nitrophenyl)piperazin-1-yl)methanone;
33) 1-((2R,3R)-3-(2,4-Difluorophenyl)-3-hydroxy-4-(1H-1,2,4-triazol-1-yl)butan-2-yl)-N-(4-fluorophenyl)-3-methyl-1H-pyrazole-4-carboxamide;
34) N-(4-Chlorophenyl)-1-((2R,3R)-3-(2,4-difluorophenyl)-3-hydroxy-4-(1H-1,2,4-triazol-1-yl)butan-2-yl)-3-methyl-1H-pyrazole-4-carboxamide;
35) N-(4-Chlorophenyl)-1-((2R,3R)-3-(2,4-difluorophenyl)-3-hydroxy-4-(1H-1,2,4-triazol-1-yl)butan-2-yl)-N,3-dimethyl-1H-pyrazole-4-carboxamide;
36) (4-(4-Chlorophenyl)piperazin-1-yl)(1-((2R,3R)-3-(2,4-difluorophenyl)-3-hydroxy-4-(1H-1,2,4-triazol-1-yl)butan-2-yl)-3-methyl-1H-pyrazol-4-yl)methanone;
37) (1-((2R,3R)-3-(2,4-Difluorophenyl)-3-hydroxy-4-(1H-1,2,4-triazol-1-yl)butan-2-yl)-3-methyl-1H-pyrazol-4-yl)(4-(4-nitrophenyl)piperazin-1-yl)methanone;
38) (2R,3R)-2-(2,4-Difluorophenyl)-3-(4-(4-fluorophenethyl)-1H-pyrazol-1-yl)-1-(1H-1,2,4-triazol-1-yl)butan-2-ol;
39) (2R,3R)-3-(4-(4-Chlorophenethyl)-1H-pyrazol-1-yl)-2-(2,4-difluorophenyl)-1-(1H-1,2,4-triazol-1-yl)butan-2-ol;
40) (2R,3R)-2-(2,4-Difluorophenyl)-3-(4-((E)-4-fluorostyryl)-1H-pyrazol-1-yl)-1-(1H-1,2,4-triazol-1-yl)butan-2-ol;
41) (2R,3R)-3-(4-((E)-4-Chlorostyryl)-1H-pyrazol-1-yl)-2-(2,4-difluorophenyl)-1-(1H-1,2,4-triazol-1-yl)butan-2-ol;
42) (2R,3R)-2-(2,4-Difluorophenyl)-3-(4-((E)-4-nitrostyryl)-1H-pyrazol-1-yl)-1-(1H-1,2,4-triazol-1-yl)butan-2-ol;
43) (2R,3R)-2-(2,4-Difluorophenyl)-1-(1H-1,2,4-triazol-1-yl)-3-(4-((E)-4-(trifluoromethyl)styryl)-1H-pyrazol-1-yl)butan-2-ol;
44) (2R,3R)-3-(4-((E)-(3,4-Dichlorostyryl)-1H-pyrazol-1-yl)-2-(2,4-difluorophenyl)-1-(1H-1,2,4-triazol-1-yl)butan-2-ol;
45) (2R,3R)-2-(2,4-Difluorophenyl)-3-(4-(4-fluorophenyl)ethynyl)-1H-pyrazol-1-yl)-1-(1H-1,2,4-triazol-1-yl)butan-2-ol;
46) (2R,3R)-2-(2,4-Difluorophenyl)-3-(4-(2,4-difluorophenyl)ethynyl)-1H-pyrazol-1-yl)-1-(1H-1,2,4-triazol-1-yl)butan-2-ol;
47) (2R,3R)-2-(2,4-Difluorophenyl)-3-(4-((4-fluoro-3-methylphenyl)ethynyl)-1H-pyrazol-1-yl)-1-(1H-1,2,4-triazol-1-yl)butan-2-ol;
48) 4-((1-((2R,3R)-3-(2,4-Difluorophenyl)-3-hydroxy-(4-(1H-1,2,4-triazol-1-yl)butan-2-yl)-1H-pyrazol-4-yl)ethynyl)benzonitrile;

49) (2R,3R)-2-(2,4-Difluorophenyl)-3-(4-(4-fluorobenzyl)-1H-pyrazol-1-yl)-1-(1H-1,2,4-triazol-1-yl)butan-2-ol;
50) (2R,3R)-3-(4-(4-Chlorobenzyl)-1H-pyrazol-1-yl)-2-(2,4-difluorophenyl)-1-(1H-1,2,4-triazol-1-yl)butan-2-ol;
51) (2R,3R)-2-(2,4-Difluorophenyl)-3-(4-((E)-2-(pyridin-2-yl)vinyl)-1H-pyrazol-1-yl)-1-(1H-1,2,4-triazol-1-yl)butan-2-ol;
52) (2R,3R)-2-(2,4-Difluorophenyl)-3-(4-((E)-(2-(pyridin-3-yl)vinyl)-1H-pyrazol-1-yl)-1-(1H-1,2,4-triazol-1-yl)butan-2-ol;
53) (2R,3R)-2-(2,4-Difluorophenyl)-3-(4-((E)(2-(pyrazin-2-yl)vinyl)-1H-pyrazol-1-yl)-1-(1H-1,2,4-triazol-1-yl)butan-2-ol;
54) (2R,3R)-2-(2,4-Difluorophenyl)-3-(4-((E)-(2-(6-methylpyridin-2-yl)vinyl)-1H-pyrazol-1-yl)-1-(1H-1,2,4-triazol-1-yl)butan-2-ol;
55) (2R,3R)-2-(2,4-Difluorophenyl)-3-(4-((E)-(2-(5-nitropyridin-2-yl)vinyl)-1H-pyrazol-1-yl)-1-(1H-1,2,4-triazol-1-yl)butan-2-ol;
56) (2R,3R)-2-(2,4-Difluorophenyl)-3-(4-((E)-(2-(3-methyl-5-nitropyridin-2-yl)vinyl)-1H-pyrazol-1-yl)-1-(1H-1,2,4-triazol-1-yl)butan-2-ol;
57) (2R,3R)-2-(2,4-Difluorophenyl)-3-(4-((E)-(2-(6-nitropyridin-3-yl)vinyl)-1H-pyrazol-1-yl)-1-(1H-1,2,4-triazol-1-yl)butan-2-ol;
58) 5-((E)-2-(1-((2R,3R)-3-(2,4-Difluorophenyl)-3-hydroxy-4-(1H-1,2,4-triazol-1-yl)butan-2-yl)-1H-pyrazol-4-yl)vinyl)nicotinonitrile;
59) (2R,3R)-3-(4-((E)-(2-(5-Chloropyridin-2-yl)vinyl)-1H-pyrazol-1-yl)-2-(2,4-difluorophenyl)-1-(1H-1,2,4-triazol-1-yl)butan-2-ol;
60) (2R,3R)-2-(2,4-Difluorophenyl)-3-(4-(pyridin-2-ylethynyl)-1H-pyrazol-1-yl)-1-(1H-1,2,4-triazol-1-yl)butan-2-ol;
61) (2R,3R)-2-(2,4-Difluorophenyl)-3-(4-(pyridin-3-ylethynyl)-1H-pyrazol-1-yl)-1-(1H-1,2,4-triazol-1-yl)butan-2-ol;
62) (2R,3R)-2-(2,4-Difluorophenyl)-3-(4-((5-nitropyridin-2-yl)ethynyl)-1H-pyrazol-1-yl)-1-(1H-1,2,4-triazol-1-yl)butan-2-ol;
63) (2R,3R)-2-(2,4-Difluorophenyl)-3-(4-((6-nitropyridin-3-yl)-ethynyl)-1H-pyrazol-1-yl)-1-(1H-1,2,4-triazol-1-yl)butan-2-ol;
64) (2R,3R)-2-(2,4-Difluorophenyl)-3-(4-((3-methyl-5-nitropyridin-2-yl)ethynyl)-1H-pyrazol-1-yl)-1-(1H-1,2,4-triazol-1-yl)butan-2-ol;
65) (2R,3R)-3-(4-((5-Chloropyridin-2-yl)ethynyl)-1H-pyrazol-1-yl)-2-(2,4-difluorophenyl)-1-(1H-1,2,4-triazol-1-yl)butan-2-ol;
66) (2R,3R)-2-(2,4-Difluorophenyl)-3-(4-(quinolin-4-yl)-1H-pyrazol-1-yl)-1-(1H-1,2,4-triazol-1-yl)butan-2-ol;
67) (2R,3R)-2-(2,4-Difluorophenyl)-3-(4-(quinoxalin-3-yl)-1H-pyrazol-1-yl)-1-(1H-1,2,4-triazol-1-yl)butan-2-ol; and
68) (2R,3R)-3-(4-(Benzofuran-2-yl)-1H-pyrazol-1-yl)-2-(2,4-difluorophenyl)-1-(1H-1,2,4-triazol-1-yl)butan-2-ol.

5. A method for preparing the compound of formula (I) of claim 1, which comprises the steps of: allowing a compound of formula (II) to react with a compound of formula (III) in the presence of a base to obtain a compound of formula (IV); and converting the compound of formula (IV) to the compound of formula (I):

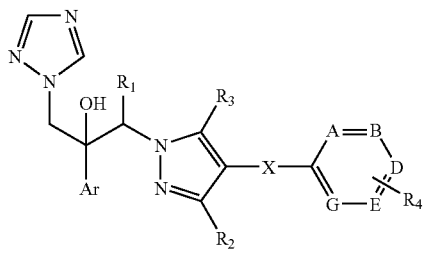
(I)

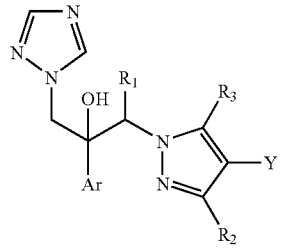
(IV)

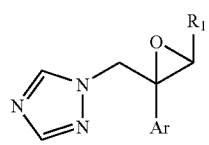
(II)

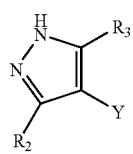
(III)

wherein, Ar, A, B, D, E, G, X, $R_1$, $R_2$, $R_3$ and $R_4$ have the same meanings as defined in claim 1; and Y is —$NO_2$, —$B(OH)_2$, —$B(OC(CH_3)_2)_2$, —CHO, Cl, Br, I, —$CH_2Cl$, —$CH_2Br$, —$CO_2H$, —$NH_2$, —COCl, —CH=$CH_2$ or —C≡CH.

6. The method of claim 5, wherein the base is an inorganic base selected from the group consisting of sodium hydride (NaH), potassium carbonate ($K_2CO_3$) and sodium methoxide (NaOMe), or an organic base selected from the group consisting of triethylamine and 1,8-diazabicyclo[5,4,0]undec-7-ene (DBU).

7. A pharmaceutical composition comprising the compound of formula (I) of claim 1, or an isomer or pharmaceutically acceptable salt thereof, and a carrier.

* * * * *